United States Patent
Watt

(10) Patent No.: US 6,566,135 B1
(45) Date of Patent: May 20, 2003

(54) ANTISENSE MODULATION OF CASPASE 6 EXPRESSION

(75) Inventor: Andrew T. Watt, Vista, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 39 days.

(21) Appl. No.: 09/679,299

(22) Filed: Oct. 4, 2000

(51) Int. Cl.[7] .......................... C12N 15/63; C12Q 1/68; C12P 19/34; C07H 21/02; C07H 21/04
(52) U.S. Cl. .......................... 435/455; 435/6; 435/91.1; 536/23.1; 536/24.5
(58) Field of Search ........................ 435/6, 91.1, 91.31, 435/455, 375; 536/23.1, 24.4, 25.3; 514/44

(56) References Cited

U.S. PATENT DOCUMENTS

| | | | | |
|---|---|---|---|---|
| 5,672,500 A | * | 9/1997 | Litwack et al. | 435/240.2 |
| 5,801,154 A | * | 9/1998 | Baracchini et al. | 514/44 |
| 5,817,462 A | * | 10/1998 | Garini et al. | 435/6 |
| 5,985,640 A | | 11/1999 | Litwack et al. | |
| 6,004,933 A | | 12/1999 | Spruce et al. | |

FOREIGN PATENT DOCUMENTS

| | | | |
|---|---|---|---|
| WO | WO-9850530 | * | 11/1998 |
| WO | WO 99/66930 | | 12/1999 |
| WO | WO 99/66945 | | 12/1999 |
| WO | WO 00/02858 | | 1/2000 |
| WO | WO 00/10979 | | 3/2000 |
| WO | WO 00/21523 | | 4/2000 |

OTHER PUBLICATIONS

Karen Pihl–Carey, Isis To Restructure As Crohn's Disease Drug Fails In Phase III, The Daily Biotechnology Newspaper, vol. 10, No. 239, pp. 1–2.*

Giorgio Palu' et al., In pursuit of new developments for gene therapy of human diseases, Journal of Biotechnology 68, (1999) pp. 1–13.*

Stanley T. Crooke, Antisense Research and Application, pp. 1–50.*

Andrea D. Branch, A good antisense molecule is hard to find, TIBS 23—Feb. 1998, pp. 45–50.*

Bratton et al., *Protein complexes activate distinct caspase cascades in death receptor and stress–induced apoptosis*, Exp. Cell. Res., 2000, 256:27–33.

Deveraux et al., *IAPs block apoptotic events induced by caspase–8 and cytochrome c by direct inhibition of distinct caspases*, Embo J., 1998, 17:2215–2223.

Dong et al., *Serine protease inhibitors suppress cytochrome c–mediatedcaspase–9 activation and apoptosis during hypoxia–reoxygenation [In Process Citation]*, Biochem. J., 2000, 347 Pt 3:669–677.

Faleiro et al., *Multiple species of CPP32 and Mch2 are the major active caspases present in apoptotic cells*, Embo J., 1997, 16:2271–2281.

Fernandes–Alnemri et al., *Mch2, a new member of the apoptotic Ced–3/Ice cysteine protease gene family*, Cancer Res., 1995, 55:2737–2742.

Garcia–Calvo et al., *Purification and catalytic properties of human caspase family members*, Cell. Death Differ., 1999, 6:362–369.

LeBlanc et al., *Caspase–6 role in apoptosis of human neurons, amyloidogenesis, and Alzheimer's disease*, J. Biol. Chem., 1999, 274:23426–23436.

Nasir et al., *Localization of the cell death genes CPP32 and Mch–2 to human chromosome 4q*, Mamm. Genome, 1997, 8:56–59.

Orth et al., *The CED–3/ICE–like protease Mch2 is activated during apoptosis and cleaves the death substrate lamin A*, J. Biol. Chem., 1996, 271:16443–16446.

Pellegrini et al., *Alternative, non–secretase processing of Alzheimer's beta–amyloid precursor protein during apoptosis by caspase–6 and –8*, J. Biol. Chem., 1999, 274:21011–21016.

Seki et al., *Cisplatin (CDDP) specifically induces apoptosis via sequential activation of caspase–8, –3 and –6 in osteosarcoma*, Cancer Chemother. Pharmacol., 2000, 45:199–206.

Soini et al., *Apoptosis and expression of caspases 3, 6 and 8 in malignant non–Hodgkin's lymphomas*, Apmis, 1999, 107:1043–1050.

Takahashi et al., *Cleavage of lamin A by Mch2 alpha but not CPP32: multiple interleukin 1 beta–converting enzyme–r–elated proteases with distinct substract recognition properties are active in apoptosis*, Proc. Natl. Acad. Sci. U. S. A., 1996, 93:8395–8400.

Thornberry, *The caspase family of cysteine proteases*, Br. Med. Bull., 1997, 53:478–490.

Tiso et al., *Chromosomal localization of the human genes, CPP32, Mch2, Mch3, and Ich–1, involved in cellular apoptosis*, Biochem. Biophys. Res. Commun., 1996, 225:983–989.

Turunen et al., *Apoptosis in gallbladder carcinomas and dysplasias, its relation to the expression of caspases 3, 6 and 8 and apoptosis regulating proteins bcl–2, mcl–1 and bax*, Histol. Histopathol., 2000, 15:53–60.

Vakkala et al., *Expression of caspases 3, 6 and 8 is increased in parallel with apoptosis and histological aggressiveness of the breast lesion*, Br. J. Cancer, 1999, 81:592–599.

* cited by examiner

Primary Examiner—Sean McGarry
Assistant Examiner—Jane Zara
(74) Attorney, Agent, or Firm—Licata & Tyrrell P.C.

(57) ABSTRACT

Antisense compounds, compositions and methods are provided for modulating the expression of caspase 6. The compositions comprise antisense compounds, particularly antisense oligonucleotides, targeted to nucleic acids encoding caspase 6. Methods of using these compounds for modulation of caspase 6 expression and for treatment of diseases associated with expression of caspase 6 are provided.

13 Claims, No Drawings

SEQUENCE LISTING

<160> NUMBER OF SEQ ID NOS: 164

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                                  20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                                  20

<210> SEQ ID NO 3
<211> LENGTH: 1313
<212> TYPE: DNA
<213> ORGANISM: Homo sapiens
<220> FEATURE:
<221> NAME/KEY: CDS
<222> LOCATION: (1)...(615)

<400> SEQUENCE: 3

```
atg agc tcg gcc tcg ggg ctc cgc agg ggg cac ccg gca gtg tca act        48
Met Ser Ser Ala Ser Gly Leu Arg Arg Gly His Pro Ala Val Ser Thr
 1               5                  10                  15 gtt agc cac gca gat gcc gat tgc ttt gtg tgt gtc ttc ctg agc cat        96
Val Ser His Ala Asp Ala Asp Cys Phe Val Cys Val Phe Leu Ser His
             20                  25                  30 ggc gaa ggc aat cac att tat gca tat gat gct aaa atc gaa att cag       144
Gly Glu Gly Asn His Ile Tyr Ala Tyr Asp Ala Lys Ile Glu Ile Gln
         35                  40                  45 aca tta act ggc ttg ttc aaa gga gac aag tgt cac agc ctg gtt gga       192
Thr Leu Thr Gly Leu Phe Lys Gly Asp Lys Cys His Ser Leu Val Gly
     50                  55                  60 aaa ccc aag ata ttt atc atc cag gca tgt cgg gga aac cag cac gat       240
Lys Pro Lys Ile Phe Ile Ile Gln Ala Cys Arg Gly Asn Gln His Asp
 65                  70                  75                  80 gtg cca gtc att cct ttg gat gta gta gat aat cag aca gag aag ttg       288
Val Pro Val Ile Pro Leu Asp Val Val Asp Asn Gln Thr Glu Lys Leu
                 85                  90                  95 gac acc aac ata act gag gtg gat gca gcc tcc gtt tac acg ctg cct       336
Asp Thr Asn Ile Thr Glu Val Asp Ala Ala Ser Val Tyr Thr Leu Pro
            100                 105                 110 gct gga gct gac ttc ctc atg tgt tac tct gtt gca gaa gga tat tat       384
Ala Gly Ala Asp Phe Leu Met Cys Tyr Ser Val Ala Glu Gly Tyr Tyr
        115                 120                 125 tct cac cgg gaa act gtg aac ggc tca tgg tac att caa gat ttg tgt       432
Ser His Arg Glu Thr Val Asn Gly Ser Trp Tyr Ile Gln Asp Leu Cys
```

|  |  |  |  |  |  |  |  |  |  |  |  |  |  |  |  |
|---|---|---|---|---|---|---|---|---|---|---|---|---|---|---|---|
|  |  | 130 |  |  |  | 135 |  |  |  | 140 |  |  |  |  |  |
| gag | atg | ttg | gga | aaa | tat | ggc | tcc | tcc | tta | gag | ttc | aca | gaa | ctc | ctc |
| Glu | Met | Leu | Gly | Lys | Tyr | Gly | Ser | Ser | Leu | Glu | Phe | Thr | Glu | Leu | Leu |
| 145 |  |  |  |  | 150 |  |  |  |  | 155 |  |  |  |  | 160 |

480 aca ctg gtg aac agg aaa gtt tct cag cgc cga gtg gac ttt tgc aaa        528
Thr Leu Val Asn Arg Lys Val Ser Gln Arg Arg Val Asp Phe Cys Lys
                165                 170                 175 gac cca agt gca att gga aag aag cag gtt ccc tgt ttt gcc tca atg        576
Asp Pro Ser Ala Ile Gly Lys Lys Gln Val Pro Cys Phe Ala Ser Met
            180                 185                 190 cta act aaa aag ctg cat ttc ttt cca aaa tct aat taa ttaatagagg         625
Leu Thr Lys Lys Leu His Phe Phe Pro Lys Ser Asn
        195                 200                 205 ctatctaatt tcacactctg tattgaaaat ggctttctca gccaggcgtg gttactcaca      685
cctgtaatcc cagcactttg ggagtccaag gtgggcggat cacctgaggt cgggagttcg      745
agaccagcct gaccaacatg gcagaagccc gcctctact aaaaatgcaa aaaaaattt       805 agctaggcat ggcggcgcat gcctgcaatc ccagctactt ggaaggctga ggcaggagaa      865
tcacttgaac ccaggaggtg gaggctgcgg tgagccgagc attgcgccat tgcactccag      925
cctgggcaac gagtgaaact ccgtctcaaa aaaaagaaa atgtctttct cttccttta       985 tataaatatc gttagggtga agcattatgg tctaatgatt caaatgtttt aaagtttaat    1045
gcctagcaga gaactgcctt aaaaaaaaaa agttcatgtt ggccatggtg aaagggtttg    1105
atatggagaa acaaaatcct caggaaatta gataaataga aatttataag catttgtatt    1165
attttttaat aaactgcagg gttacaccaa aatctagctg atttaacttg tatttttgtca   1225 cttttttata aagtttatt gtttgatgtt tttaaaggtt tttgaaatcc aggaattaaa    1285 tcatcccta ataaaatatt cgaaattc                                         1313

<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
aggctgaggc aggagaatca                                                  20

<210> SEQ ID NO 5
<211> LENGTH: 17
<212> TYPE: DNA
<213> ORGANISM: Artificial Sequence
<220> FEATURE:
<223> OTHER INFORMATION: PCR Primer

<400> SEQUENCE: 5
tgcaatggcg caatgct                                                     17

<210> SEQ ID NO 6
<211> LENGTH: 23
<212> TYPE: DNA
<213> ORGANISM: Artificial Sequence
<220> FEATURE:
<223> OTHER INFORMATION: PCR Probe

<400> SEQUENCE: 6
tgaacccagg aggtggaggc tgc                                              23

```
<210> SEQ ID NO 7
<211> LENGTH: 21
<212> TYPE: DNA
<213> ORGANISM: Artificial Sequence
<220> FEATURE:
<223> OTHER INFORMATION: PCR Primer

<400> SEQUENCE: 7
caacggattt ggtcgtattg g                                          21

<210> SEQ ID NO 8
<211> LENGTH: 26
<212> TYPE: DNA
<213> ORGANISM: Artificial Sequence
<220> FEATURE:
<223> OTHER INFORMATION: PCR Primer

<400> SEQUENCE: 8
ggcaacaata tccactttac cagagt                                     26

<210> SEQ ID NO 9
<211> LENGTH: 21
<212> TYPE: DNA
<213> ORGANISM: Artificial Sequence
<220> FEATURE:
<223> OTHER INFORMATION: PCR Probe

<400> SEQUENCE: 9
cgcctggtca ccagggctgc t                                          21

<210> SEQ ID NO 10
<211> LENGTH: 1229
<212> TYPE: DNA
<213> ORGANISM: Mus musculus
<220> FEATURE:
<221> NAME/KEY: CDS
<222> LOCATION: (25)...(855)

<400> SEQUENCE: 10
ctcgcgggca ggtgaaagta aaac atg aca gaa acc gat ggc ttc tac aaa    51
                           Met Thr Glu Thr Asp Gly Phe Tyr Lys
                             1               5 agt agg gaa gtg ttc gat cca gcc gag cag tac aag atg gac cac aag   99
Ser Arg Glu Val Phe Asp Pro Ala Glu Gln Tyr Lys Met Asp His Lys
 10              15                  20                  25 agg aga gga gtt gcc ctc atc ttc aat cac gag agg ttc ttt tgg cac  147
Arg Arg Gly Val Ala Leu Ile Phe Asn His Glu Arg Phe Phe Trp His
             30                  35                  40 ctg acc ctc cca gag agg cgg ggc acc aac gca gac aga gac aac ctg  195
Leu Thr Leu Pro Glu Arg Arg Gly Thr Asn Ala Asp Arg Asp Asn Leu
         45                  50                  55 act cgc agg ttt tca gat cta gga ttt gaa gtg aaa tgc ttt aac gac  243
Thr Arg Arg Phe Ser Asp Leu Gly Phe Glu Val Lys Cys Phe Asn Asp
     60                  65                  70 ctc aga gca gaa gaa ctc ctg ctc aaa att cac gag gtg tcg act tca  291
Leu Arg Ala Glu Glu Leu Leu Leu Lys Ile His Glu Val Ser Thr Ser
 75                  80                  85 agc cac ata gat gcc gat tgc ttc atc tgt gtc ttc ctg agc cat ggg  339
Ser His Ile Asp Ala Asp Cys Phe Ile Cys Val Phe Leu Ser His Gly
 90                  95                 100                 105 gaa ggc aac cac gtt tac gca tac gac gcc aaa att gaa att cag acg  387
Glu Gly Asn His Val Tyr Ala Tyr Asp Ala Lys Ile Glu Ile Gln Thr
                110                 115                 120 ttg act ggc ttg ttc aaa gga gac aag tgt cag agc ctg gtt gga aaa  435
```

```
Leu Thr Gly Leu Phe Lys Gly Asp Lys Cys Gln Ser Leu Val Gly Lys
        125                 130                 135 ccc aag ata ttt atc atc cag gcc tgt cgg ggt agc cag cat gac gta    483
Pro Lys Ile Phe Ile Ile Gln Ala Cys Arg Gly Ser Gln His Asp Val
        140                 145                 150 ccc gtg gtt ccc ctg gac atg gtg gat cac cag aca gac aag ctg gac    531
Pro Val Val Pro Leu Asp Met Val Asp His Gln Thr Asp Lys Leu Asp
        155                 160                 165 aac gtg acc cag gtg gat gct gcg tcc gtg tac acg ctg ccg gca ggg    579
Asn Val Thr Gln Val Asp Ala Ala Ser Val Tyr Thr Leu Pro Ala Gly
170                 175                 180                 185 gca gac ttc ctc atg tgc tac tct gtc gca gaa ggg tat tac tct cac    627
Ala Asp Phe Leu Met Cys Tyr Ser Val Ala Glu Gly Tyr Tyr Ser His
                190                 195                 200 cga gaa act gtg aat ggc tcc tgg tac att cag gat ttg tgt gag atg    675
Arg Glu Thr Val Asn Gly Ser Trp Tyr Ile Gln Asp Leu Cys Glu Met
            205                 210                 215 ctg gcg agg tac ggc agt tcc ctg gag ttc acg gag ctg ctc acg ctg    723
Leu Ala Arg Tyr Gly Ser Ser Leu Glu Phe Thr Glu Leu Leu Thr Leu
        220                 225                 230 gtg aac aga aag gtc tct cag cgc cgc gtg gac ttc tgc aaa gac ccg    771
Val Asn Arg Lys Val Ser Gln Arg Arg Val Asp Phe Cys Lys Asp Pro
    235                 240                 245 gat gca atc ggc aag aag cag gtg ccc tgc ttc gcc tca atg ctg acc    819
Asp Ala Ile Gly Lys Lys Gln Val Pro Cys Phe Ala Ser Met Leu Thr
250                 255                 260                 265 aaa aag ctg cat ttc tgt ccc aaa cct agc aag tag ggccatctgt         865
Lys Lys Leu His Phe Cys Pro Lys Pro Ser Lys
                270                 275 cttgctacat atatttcaca cacatttccc tttttataca aaggccagct ggtggaagac    925
tttcacccat caatgtaaac tgcttcaatt ttgtagatgc catagaaaag taatgtttta    985
tatttgttac ttttcaatca tgttggacgt ggtggaaggg ctaaaaataa tcctcaggaa   1045
attactatgc atcaatgtct actacattta ttacattttt agtaaactgt aagattactc   1105
taaataccaa ctactttgcc tcccctttg tgacactgtt tatatgagtt tactgtataa   1165
tgtttgtaaa gacttttgaa actctagact gagattgttt tcgcgtaata aaatgtctaa   1225
gaac                                                                1229

<210> SEQ ID NO 11
<211> LENGTH: 20
<212> TYPE: DNA
<213> ORGANISM: Artificial Sequence
<220> FEATURE:
<223> OTHER INFORMATION: PCR Primer

<400> SEQUENCE: 11
agcatgacgt acccgtggtt                                                 20

<210> SEQ ID NO 12
<211> LENGTH: 21
<212> TYPE: DNA
<213> ORGANISM: Artificial Sequence
<220> FEATURE:
<223> OTHER INFORMATION: PCR Primer

<400> SEQUENCE: 12
ggtcacgttg tccagcttgt c                                               21

<210> SEQ ID NO 13
```

```
<211> LENGTH: 25
<212> TYPE: DNA
<213> ORGANISM: Artificial Sequence
<220> FEATURE:
<223> OTHER INFORMATION: PCR Probe

<400> SEQUENCE: 13
ccctggacat ggtggatcac cagac                                          25

<210> SEQ ID NO 14
<211> LENGTH: 20
<212> TYPE: DNA
<213> ORGANISM: Artificial Sequence
<220> FEATURE:
<223> OTHER INFORMATION: PCR Primer

<400> SEQUENCE: 14
ggcaaattca acggcacagt                                                20

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
gggtctcgct cctggaagct                                                20

<210> SEQ ID NO 16
<211> LENGTH: 27
<212> TYPE: DNA
<213> ORGANISM: Artificial Sequence
<220> FEATURE:
<223> OTHER INFORMATION: PCR Probe

<400> SEQUENCE: 16
aaggccgaga atgggaagct tgtcatc                                        27

<210> SEQ ID NO 17
<211> LENGTH: 1545
<212> TYPE: DNA
<213> ORGANISM: Homo sapiens
<220> FEATURE:
<221> NAME/KEY: CDS
<222> LOCATION: (79)...(960)

<400> SEQUENCE: 17
ccgagggcgg ggccgggccc gggagcctgt ggcttcagga agaggagggc aagtgtctg     60 gctgcgcgtt tggctgca atg agc tcg gcc tcg ggg ctc cgc agg ggg cac    111
                     Met Ser Ser Ala Ser Gly Leu Arg Arg Gly His
                      1               5                  10 ccg gca ggt ggg gaa gaa aac atg aca gaa aca gat gcc ttc tat aaa    159
Pro Ala Gly Gly Glu Glu Asn Met Thr Glu Thr Asp Ala Phe Tyr Lys
             15                  20                  25 aga gaa atg ttt gat ccg gca gaa aag tac aaa atg gac cac agg agg    207
Arg Glu Met Phe Asp Pro Ala Glu Lys Tyr Lys Met Asp His Arg Arg
         30                  35                  40 aga gga att gct tta atc ttc aat cat gag agg ttc ttt tgg cac tta    255
Arg Gly Ile Ala Leu Ile Phe Asn His Glu Arg Phe Phe Trp His Leu
     45                  50                  55 aca ctg cca gaa agg cgg cgc acc tgc gca gat aga gac aat ctt acc    303
Thr Leu Pro Glu Arg Arg Arg Thr Cys Ala Asp Arg Asp Asn Leu Thr
 60                  65                  70                  75
```

```
cgc agg ttt tca gat cta gga ttt gaa gtg aaa tgc ttt aat gat ctt     351
Arg Arg Phe Ser Asp Leu Gly Phe Glu Val Lys Cys Phe Asn Asp Leu
            80                  85                  90 aaa gca gaa gaa cta ctg ctc aaa att cat gag gtg tca act gtt agc     399
Lys Ala Glu Glu Leu Leu Leu Lys Ile His Glu Val Ser Thr Val Ser
        95                  100                 105 cac gca gat gcc gat tgc ttt gtg tgt gtc ttc ctg agc cat ggc gaa     447
His Ala Asp Ala Asp Cys Phe Val Cys Val Phe Leu Ser His Gly Glu
            110                 115                 120 ggc aat cac att tat gca tat gat gct aaa atc gaa att cag aca tta     495
Gly Asn His Ile Tyr Ala Tyr Asp Ala Lys Ile Glu Ile Gln Thr Leu
        125                 130                 135 act ggc ttg ttc aaa gga gac aag tgt cac agc ctg gtt gga aaa ccc     543
Thr Gly Leu Phe Lys Gly Asp Lys Cys His Ser Leu Val Gly Lys Pro
140                 145                 150                 155 aag ata ttt atc atc cag gca tgt cgg gga aac cag cac gat gtg cca     591
Lys Ile Phe Ile Ile Gln Ala Cys Arg Gly Asn Gln His Asp Val Pro
            160                 165                 170 gtc att cct ttg gat gta gta gat aat cag aca gag aag ttg gac acc     639
Val Ile Pro Leu Asp Val Val Asp Asn Gln Thr Glu Lys Leu Asp Thr
        175                 180                 185 aac ata act gag gtg gat gca gcc tcc gtt tac acg ctg cct gct gga     687
Asn Ile Thr Glu Val Asp Ala Ala Ser Val Tyr Thr Leu Pro Ala Gly
        190                 195                 200 gct gac ttc ctc atg tgt tac tct gtt gca gaa gga tat tat tct cac     735
Ala Asp Phe Leu Met Cys Tyr Ser Val Ala Glu Gly Tyr Tyr Ser His
205                 210                 215 cgg gaa act gtg aac ggc tca tgg tac att caa gat ttg tgt gag atg     783
Arg Glu Thr Val Asn Gly Ser Trp Tyr Ile Gln Asp Leu Cys Glu Met
220                 225                 230                 235 ttg gga aaa tat ggc tcc tcc tta gag ttc aca gaa ctc ctc aca ctg     831
Leu Gly Lys Tyr Gly Ser Ser Leu Glu Phe Thr Glu Leu Leu Thr Leu
            240                 245                 250 gtg aac agg aaa gtt tct cag cgc cga gtg gac ttt tgc aaa gac cca     879
Val Asn Arg Lys Val Ser Gln Arg Arg Val Asp Phe Cys Lys Asp Pro
        255                 260                 265 agt gca att gga aag aag cag gtt ccc tgt ttt gcc tca atg cta act     927
Ser Ala Ile Gly Lys Lys Gln Val Pro Cys Phe Ala Ser Met Leu Thr
        270                 275                 280 aaa aag ctg cat ttc ttt cca aaa tct aat taa ttaatagagg ctatctaatt   980
Lys Lys Leu His Phe Phe Pro Lys Ser Asn
285                 290 tcacactctg tattgaaaat ggctttctca gccaggcgtg gttactcaca cctgtaatcc  1040
cagcactttg ggagtccaag gtgggcggat caccctgagg tcgggagttcg agaccagcct 1100 gaccaacatg gcagaagccc cgcctctact aaaaatgcaa aaaaaaattt agctaggcat  1160
ggcggcgcat gcctgcaatc ccagctactt ggaaggctga gcaggagaa tcacttgaac   1220 ccaggaggtg gaggctgcgg tgagccgagc attgcgccat gcactccag cctgggcaac   1280 gagtgaaact ccgtctcaaa aaaaagaaa atgtctttct cttccttta tataaatatc    1340 gttagggtga agcattatgg tctaatgatt caaatgtttt aaagtttaat gcctagcaga  1400
gaactgcctt aaaaaaaaaa agttcatgtt ggccatggtg aaagggtttg atatggagaa  1460
acaaaatcct caggaaatta gataaataaa aatttataag catttgtatt atttttaat   1520 aaactgcagg gttacacaaa aatct                                         1545

<210> SEQ ID NO 18
<211> LENGTH: 17000
```

<212> TYPE: DNA
<213> ORGANISM: Homo sapiens

<400> SEQUENCE: 18

```
ttaagggaat gttgtggctg tttttatctt ctatccagac caactagaac tttctccata        60
tcagcaataa ggctgtttag ctttattgtc ttttgtgtgt ttactggagt agcatttta        120
atttccttca aaattttttc ctttgcattc atgacttggc ttttctcctt tgcactcaca       180
acttggctaa ctggagcaag aagcctagct ttctgcctac caacattact tcctcactaa       240
cttaatcatg tttgcttttg atttaaagtg acaggctctt cctttcattt ggacacttag       300
aggcctttgt aggattatta gttggcctaa tttcaaaatt gtgtttccag gaatagggag       360
gccccaggag ggggagagag aagggaaagt tcggtggaac agtccaaaca catacagggc       420
ttatggatta atttcccctt cctttatgag cgcggttcat ggtgccccaa acaattgca        480
ataatattaa agattactga tcacagatca aacagcaga cataataaca atgaaaaatt        540
ttgaaatatt gcgagagtac caaaatgtga cacagagaca caaagcgagc caatgttgaa       600
atacaggcag tatctgctaa gcggtataaa acaatctatg cctgtacctc tagaaagtac       660
aggcatagca aagtaaggaa tagcaaatgt ttggggcagc tgggattaaa tgagtccgag       720
ctcacacaag tgatgtgaaa ttgcctcggg ctaggcggtc tgtgtgtccc ccgggtggc        780
aactggcatg tccccagggc acggttagtc ccagcgggcc tggaggcgaa gaccgcgtac       840
ctctccctgc ccccgcgctc ttggtccccg cgggctccgg agcgactggg aggagcttta       900
actctgggaa ggaccagccc gatccacggg agcccgggcg gcgcgcaatc agaaccaact       960
ggccccacgc tcggggcag ggggcgggc cgccgaggaa gggccgaggg cggggccggg        1020
cccgggagcc tgtggcttca ggaagaggag ggcaaggtgt ctggctgcgc gtttggctgc      1080
aatgagctcg gcctcgggc tccgcagggg gcacccggca ggtaggcagg gggcgtcgac       1140
tgggcaccga gcaggtctgc gtcttgctcc ggctggaggg gaaacgaggg ttagtggacc      1200
gggcgcgcgg accggagtgg ggccgcgggt tccttcggct ttgcagggcg gcctggagaa      1260
gttgcactct tggattgaag cgctcaggc gggtggggac ggtttcgcgc ttcagtctaa       1320
gaaacactcg gggacctggc tgccgcctcc tggcggtccc gagtagcgac gccggcgccg      1380
gggcgtgccc ctgccgcctt tgtcctccgg ggcgatgagc gctttcgggg cgccccggct     1440
gtttaaacct taaaggctg tccccacgcg ggcctggcgt tccccacac ctggccgttt       1500
gaaatgttgg gggttggatc ttttgttttgc tcacttcgaa aagtgaaaag gagggggttgt     1560
tccgccgagt cataatgaaa acataacagg cccgcgggt gcccgggcca agaccctggg       1620
tcctcccggg cttcagctgg aggcggccag ttcctggcgg ccagcacacc ccggtatctc      1680
tcttcttcat ccaggaaacc tgctgctgtc tgtcggtttg agccaaaacc acaataactt      1740
ttttctgcaa agtaatcaac tgctaagagc gtacgttctg tcacttatta ctggtaaagt      1800
ttagaaactt caagcctggc cagagtgaaa caaacaaaaa ggtcgaaacg cctgcagttg      1860
gccggccgtg gtggctcacg ccttgtaatc ccaacacttt gggaggccga ggcggcgga       1920
tcaccagagg tcgggagttc tcgaccagcc taactaacac ggtgaaaccc cgtctctact      1980
aaaaatacaa aaaattagc caggcctggg cgcaagctac tggggaggct gagacaagag      2040
aatcgtttga accctggagg tggaggttgc agtgagccga gatcgcccca ctgcactcca     2100
acctcggcga cagagtgaga cttcgaatca agaagaaaaa aaaaaaaaaa gaacgaaacg      2160
cctgcagttg gttagagtgc ctttgtttaa gaactcttta tattttgctg cacaaaggaa      2220
```

-continued

```
atggtgctcc agaggcaagc tgtaaaagtc acatggtcgt agaggaggta gataggtagc    2280
cttgtcctgg aggcacagtg cagggtccag ttgcagtctc tagggcgggg aagccggggc    2340
tttccttcac tcacctgctc ccttcctctt cttcctccac cgcactcccc agtgcatgtt    2400
ctaggcctga tggaggttac tctacatagg gttactaaat acattgttga tggagccgat    2460
gggtagattt tcatagagag tgcagtgaat gaagacgatg acagtagaat gaccgaagtc    2520
gtttgggaag ttgaacaaag tttagaaagg tagccggtct cgggtgggag gggctgcgtg    2580
gggatgggcc tacagagact ttggaatctg taggtgggct ggctttcaat cccagcttca    2640
ctttgccgac cttggcacgc ctggcccact ttctctgtcc ctgttcctga gctgtggagc    2700
tgtgagataa ggtatctaag gcatcaggcc atcaacaaat ggtagctggc aggattatct    2760
ggagggacta tcaaattaga gtgaggtgaa aaaaggaatg attagttttg taaaacctaa    2820
gctgatttaa ggaataagga ggtggcagtt acattatcct gcaaaggaag agaagtgaaa    2880
agagggccag acacagtggt gggcgcctct agtcccagct actggggaga ctgaggcagg    2940
agaatcgctt gaaacctgga ggtggacttg cagtgagcca agattgcgcc actgcactgc    3000
agcctgggcg acagagggag gctctgtctc aaaaaaaaaa agtgaaaaga ggtcaagaat    3060
caggtttaaa gaagggcaca ttttttgataa gtagattgca gatgaaaagg aatttctata    3120
tctgttatac agggtagctc cttcattaaa atttattttc tccatatcaa taaagctatt    3180
tcttacttta tccaggtttt taaatattaa cgcaggccgg gcgtggtggc tcatgcttgt    3240
aatcccagca cttccaggag gctgaggcag gtggatcact tgaggccagg agttcaagac    3300
cagccaggac aacatagcaa aaccctgtct ctactgaaaa tacaaaaaaa aagtagctgg    3360
gtgtggtggc gcatgcctgt aatcccagct actcaggagg ctgaggcggg agaatcgctt    3420
gaacccggag gcggaggttg tggtgagccg agaccacgcc actgcactcc agcctaggca    3480
acagagcaag actccatccc aaaaagatag taataaaaaa taatattaa tgcggcataa    3540 tgatacttaa gtgccccctt ctggaaagct tgtcttcttg ggatacacag ctcaaggtgg    3600
tcatgatgtg ttattttctc tcaatctgtg ggtaaagttt atcaactcca gaaagtatt    3660 ggaacttagg tcctggcatc tgtctccata gcttttttgtt ctgattcagt gtttgctaga    3720
gtggccactg gacctggtca ttaactggta ctgcaggatg cagggtgcac tttgtgagag    3780
tgaaggtaag ttacagctgg ccagcatcag aattgggatg tccagagcct aggttttttt    3840
ctacatccgt agcattaaca aacaacaaca acaacaaaaa acttaaaaaa aaatccctc    3900 actgaggttg ccaaatctgt taactttgaa actgaatgta ttaagagatg gggtctagct    3960
ctgttaccca ggctggagta tggtgactat tcacaggggc agtcatagca cactatgtcc    4020
tagaactctt gggctcaaga gatcctcctg ccttggcctt ccaggtaacc gggactatag    4080
gcttgccact atgcccggcc agaacgtcat ttttaaacaga ttttcttgag cagctactta    4140
atactagtta gccattccta aacctgtagg tcttgactaa tgtgagggca tatttgagac    4200
aacccaaact cacatcttaa gttattaatt ttaatgtgtc agctaacaac tgggaagcta    4260
cttctttggc aatatgagaa acaagagttt taaagaccca agcaagaata catctccagt    4320
gttttcaccc tgagggatat gagttagttt gctgagcagc catttggcac agcttccatg    4380
agttaggttg tgagccgcct tcggctcagc agtcagtatg gagcagaagc cacaggaggt    4440
gagccgctgg cctgctgcca ccgaggagga cactgagaca tgagtgcttt ccaagttgtg    4500
cagaattttg gcatgtgagg aggatggttg tgacatatgg atttaatttt cttgaagtta    4560
ttgtttcttt atactctaat tggttaaaag ataagcaggt gaggttatca aaaggcagta    4620
```

```
gattccgaca gcttttgaaa atgggaagag tgaaatccct gtgctgtctt catagagcag   4680
tgtgtggagt aggaagtacc tcgttactgt gctcacctag gcaaaggtc ggattaaaca    4740 gctttctcat ctgccatgca gcgggagga ccagttggag aggttgcttt tggctctcac    4800
accttagtgt aaaaatcact ttgtgaaaaa tgcagctgtc acctccttcc tccaagattc   4860
tgattctgcc tcagttagga tccaggaatc tgcattttaa catgcacacc aggaattctg   4920
atgcccaagg ttgagcaaaa ctgacttagg gcgtacagac agaggatgcc ttagtgtggg   4980
gtcttagttg ggtctcattg cttggggcag ttccaggagg aataggctaa aagggacttg   5040
aactgaattc cccaccttgt atttttttg aggagaagtg aggttagatc aatcaggtga    5100
tgggggctag taatggggag atctctaagg agagggaac caaccctttt ggctaggaga    5160
tgatgggtaa gagtccatgc tttagggtca ttcttcctca actgaagggt gcatcttgct   5220
atactgctaa tatttcagtt tattcattgc tgtctcccct ctaagctgtt gagctatcag   5280
gtaaaaacag atgcatgagt ggatgggggcc tttattgtag aagatgccac actttgcact  5340
gtccagtgta aagccactg gccaattcat ttaaattgac aataaaatcg agttcctcag    5400
ttgcattagc tgcatttaaa tgctcagtag acacatgtgg ccagtggcta ccttatgaga   5460
cagtgcaaat acgaacaat tccaccatca cagacacttc catgacatag cactgctcta    5520
gagagtagag aggaattcag tggaaggctg tccagggagt agggagtcca gttgagaatg   5580
gagagcagag ggctcccctt acagggttgg aaatgcagat gtgtcatgca ggagatccaa   5640
ggtccaagtc tttgcccttg cccttccctt cctccaccca aacttctacc tcttccaggc   5700
ttacaccact gctaatccag cattaaccac aaactatatt tcagttttcc tgtaggactt   5760 aattctttt cagaaaatgt gcaaaaacat tttctgcata acaaagcaac ttcatatttc    5820
aactccgtaa tcacagaact gttactctag gcatattttg cagtgaatgc atttgtgtaa   5880
tattttctcc atttctgttt ataagattgt tattttgcag gtcaagttgg gggtgagaaa   5940
gcatagagct gttatagttt gtttattagt aagcagtttc ccttcatttc cttttcttca   6000
catactttgg cttttaaact aaccaaaaca gaagggtctt aagagtttgg gagtcagaag   6060
ggggatggga gttcctacta tattttactg ccataagtaa aaaataatta acaaaaatca   6120
acttttttta ataggtgggg aagaaaacat gacagaaaca gatgccttct ataaaaggta   6180
aagctgtgct cttttctaat aaaggtctct tcctttgatg gtcatgatca gcctacagaa   6240
atcaaagcaa gaatgggtcc tgggagctag gaagtaaaac tgagtaggcc aagttttagc   6300
ctttggggag ctcatttgta gataggcagg ttgtgctgcc cctggttgtc gagggacccg   6360
gagtgatgtt cagaatgcat attaattggc atggcatgag cctagagcta gaacttggtt   6420
ctgagcctcg tggttattcc tggttgctgg atcctggggg ccaggggaaa gacatcaagg   6480
cagagggtta gggatgtgtc aggatggcac atggctgctc tttaccaatt ggcagagaga   6540
tatttcagga ctttccttat tagcatggcc tttcctggag cacacccatg aacatcagc    6600 ctggcaagga ggaagctcag atctctatct acatgttgac ctagaacttg gaggggctca   6660
ttatttaata tgacttgaag tgattgtttt tcaacttttc attaacagag aaatgtttga   6720
tccggcagaa aagtacaaaa tggaccacag gaggagagga attgctttaa tcttcaatca   6780
tgagaggttc ttttggcact taacactgcc agaaaggcgg ggcacctgcg cagatagaga   6840
caatcttacc cgcaggtagt agtttttatct acctatcaag atgaggcagt taagtgataa   6900
aattactttt ggccaggtgt ggtggttcat gctggtaatc ccagcacttt gggaagccaa   6960
```

```
ggtgggagga tcacttaagg caaggagttt gagacaagtc tgggcaacag agtgagacct    7020
ggtctctaca aaaataaaa atcaattagc tgggcatggt ggcggtagtc ccagctactc    7080
tggaggctga agggggagga ttgcttgatc ccaggagttc aaggctgcac ggagctgtga    7140
tcatgccact gcactccagg ctgggcaaca gagtgagacc ttgtctctaa aataaaaaat    7200
aaaataattt ttttccatgt ttccaaatga aaagttaaaa aaaattaaaa attaaaaaaa    7260
ttccagactt ctagatgtag ggaaaagtta cttatcataa cttgtcaaca ctaatgaggt    7320
aacaacagat caagagtgtt ggagcatggg ccttgctttg atgcagcctc ccttaagaac    7380
ttgcctgagt tggccgggca tggtggctca ctcctgtaat cccggcactt tgggaggctg    7440
aggcgggtgg atcataaggt caggagattg agaccatcct ggctaacatg gtgaaaccct    7500
gtctctccta aaaatacaa aaaattagcc gggcgtggtg gtgggagcct gtagtcccag    7560
ctactcggga ggctgaggca ggagaatggc atgaagccag gaggcggagc ttgcagtgag    7620
ccaagatcaa gccactgcac tccagcctgg gcgacagagt gagcctctgt ctcaaaaaaa    7680
aaaaaaaaaa aaaacttgc ctgagttatt ttccttactc tgttctatta aatgttgaca    7740
ggcttttgca tttgtactaa catttgcata gtagacaaca acactctaaa ttgaatcggc    7800
tgtcattatg attaaatcct ttccgaccat ggtgaatgaa gggaaaacca ccattgttat    7860
atttcatttc ttttctccta aagaaagcaa atttatgtgt cgttaaaatg tgtatagatt    7920
cttccaaagt aagggtattt gacaactttg aaaagtttat aggctaacat ttcatttaat    7980
ataccactag gttttcagat ctaggatttg aagtgaaatg cttttaatgat cttaaagcag    8040
aagaactact gctcaaaatt catgagggta ggtagttttg ctatcatata gttcatcttc    8100
ctctaatgaa accgagtcct ttatcctatc tgtaaagaca ggtacaagta attacttgtg    8160
tgacaaaaa agtattaatt tagcacaggt tacaggtttt gggtatgctg ctgtgtttcc    8220
gttacccagc acatttagag acccttgcaa ataattatgc ctctaaagtt tatatttagc    8280
ataccactag ttacagtctc ttgtagaaat gaatgaaatg accccttcaa ttggcagtaa    8340
aagcctaaaa tgcaagtact acaggtgctg ggcagtcaac aggctcattt tctcattgac    8400
tcctttcatg cctcattttc tcactggttt ccaaatagtg ttggtttaca tacattacct    8460
cctttaattc tcacagcgtc aatagggggt aggtattcta attataacaa cctatattat    8520
aatcatcgct gcatgccaac cattatattt gcataattac tttaaacttt cttcagagct    8580
cttctttaaa ctgcacatca ttctaacttt ggctgctttt accagctttt ctactttgct    8640
cagaagcttt ggaggacatc agtctcatgg caccgcacct ggctttgagt actcttttgg    8700
aagctctaag tgctataatc ttttttttttt tttttgaga tggagtctcg ctgtccgccc    8760
caggctggag tgcagtggtg tgatctcagc tcactgcagc ctccacctcc tgggttcaag    8820
caattctcct gcctcagctt cccaggtagc tcgcccccat gcccagctaa ttttttgtatt    8880
tttagtagag atggggtttc accgtgttgg ccaggctggt cttgaacact ggcctcaagt    8940
gatccacctg cctcggcctc ccaaaatgct gggattccag cgtgagcca ctgcgcctgg    9000
ccctaagtgc tgtattccta tagtgaaagt gcagcaatgc gtggggagct gttgagcagc    9060
agttctgggg tctttccact ctgctctaag gtctctgctg attcaaggaa attttttagtt    9120
tattgccaaa ataacttgga tcttaagtga gattccctat cgtaatccct ttatgttttc    9180
cacatcattc tgtgttttag aaaggctaat gaaatttggt caaactctat tactctgaac    9240
tttaataaat ttggattttt ttaaaaaaat aagatacagt acggtatatt gtttgattaa    9300
agactaagtt gtttcatcac agatatttta cacttattaa agagtaggcc gggcatggtg    9360
```

```
gctcatgcct gtaatcccag cactttggga ggctgaggcg aggtggatca cctgaggtca    9420
ggagttcgag actagcctgg ctacatggca aacccccgtc tctactaaaa atacaaaaat    9480
tagctggata tggtttcaaa tctgtaatcc cagctacttg ggaggctgag gcaggagaat    9540
cgcttgaacc cgggaggtgg aggttgcagt gagccaagat cgcgccactg cactccagcc    9600
ctgggcacca agagtgaaac tctgtctcaa aaaacaaaa aagacaaaac cacaaatttt     9660
cctcctcccc aatcatgtgg atgtaacttt attcttgtgt taataaactg aattttatg     9720 tgtagataac aagcatcata ttttcatttc tatattctct tttgggtcct ttatagtgtc    9780
aactgttagc cacgcagatg ccgattgctt tgtgtgtgtc ttcctgagcc atggcgaagg    9840
caatcacatt tatgcatatg atgctaaaat cgaaattcag acattaactg gcttgttcaa    9900
aggagacaag tgtcacagcc tggttggaaa acccaagata tttatcattc aggtaagact    9960
gagtacatta tcatcttaat tataaagtct gtcattctga acatgtgata aaggtctaaa   10020
agccagtttt gaaagtaact ttctccagta attggacagg ccgttttgga attctggcca   10080
atcatagttg cactttgagc tgttagtaat aattctttga cactctcatt gtctatatta   10140
caaaataaca gcatttggat tgagatttga agtgactcac aaagtaacca atgtgctact   10200
ccctgtccga gcctgatacc aaggagagcc attggaaagc gtacctgctg attgaagagt   10260
gccgcacaag gcaacctcat cagactaggt ttgcttcttt gggaggtgga gagcatataa   10320
accagtggaa agaatggaaa aataaagcct tctagtctta tcctgtctca tcccttcac    10380 attgccccct aaaccaagat tgtttccccg ctgccaaatt ggttttaggg ataaaagtat   10440
tttttacagg cgtgatggct cacacctgta atcccagcac tttgggaggc cgaggcaggc   10500
agatcacctg aggagttcaa gaccagcctg gcaaacatgg tgaaaccctg tctctactaa   10560
aaatacaaaa attagctggg catggtggca ggtgcctgta atcccagcca ttcgggaagc   10620
tgaggcatga gaattgcttg aacctgggag gcagaggctg tagttagccg agagcatacc   10680
actgcactcc agcctgggcg tcagagcgag actctgtcta aaaaaaaaaa aaatttttt    10740 tttttgcatg aatattactt ggcacatcat taacgatttt tttttttttt ttgagatgga   10800
gtctcgctct gtcccccagg ctggagtgca atggtgcaat ctcggctcac tgcaacctcc   10860
gcccccaggt tcaattattc tcccacttca gcctcccgag tagctgggat tacaggcacc   10920
tgccatcatg gctggctaat ttttgtattt tcatagagat ggggtttcac catgttggct   10980
agtgtggtct tgaactcctg acctcaggtg atctgcccgc cttggcctcc cagagtgttg   11040
ggattacagg cgtgagccac tgtgcccggc caaagatttt gaactacaaa agagaaacct   11100
gacatgccag tgtcacaatt ctgtatttcc atgaatagca tggaggacat gaaataacat   11160
tatgttagtc tattcttgca ttgctataaa gacctgagac tgggtaattt ataaggaaga   11220
gagatttgat tggcctacag ttctgcaggc tgtacaggaa gcatggtgct ggcatctgct   11280
tctggtgagg ccttaggaag cttacaatta tggtggaagg tgacagagag ccagcatatg   11340
acttgttggg agtgggagca agagagtgcc aagggagagg tcccagactc tcttaagtaa   11400
ccagatttca tgtgaactga gtgggagctc acttacacca agaggatgat gctaaaccat   11460
tcatgagaga ccctcccccga tgatccagtc accttccacc aggcttcacc tcccacactg   11520
ggaaccacat tttaacatga gatttggagg ggacagacgt tcaaaccgta tcaaacatga   11580
aactgcattt cgcatcctac cataaagcct tgttttgggg tgaggaagtg gctgtaagtg   11640
aagaatgact gcctcgtttc tggtttggac aactgcattg gaatgtctgt gggacatgga   11700
```

```
attggtcata caggtgtaga acctaagaca ggtggcctcg gctggagaaa taaatcagga    11760
ggtggtcgtg gaagccatgg gattagatga gtttactcgt gttgaataca gcctgaaaaa    11820
ggagcataaa acaaaaccga ggggcaccca tgaggaatgg gctgaagagg gaagatactg    11880
aggaggatgg acaccaggag agaaacaaga aacaaataat gacatgattg ttttgtgaaa    11940
aggggagtgg ccaacactgt caaacacaag agaattggaa ataactaatg agctactgtg    12000
ggaagaaagc cacaaatgaa atcgttttcc aagttacttt ctctctctat gccttagatt    12060
cttggtaaaa agagcacctg cctcatgggg tggttgtgtg ggcaaaatca cctgactgat    12120
ttaatgaatg caaaccactt agaacagtgc ctggcataca gcacgccctc agtaaaggct    12180
cgctcttact cttattgcag ttgactgggc aggtgatgtc attaggttaa aggtgttctg    12240
ttatatttag gaaggacagt agaaaaaagg cctgaaaata agcctgctga tacgaagatt    12300
aaaatctgcc tataaaaacg ggatagtagg gattttctat ttattttatg atttgaaatc    12360
attcaggact ttcttttgat gctcataatt ctttaaccat ttcagaactg attgatgcat    12420
ttataatgct acaacagaat cttattggct ggctgtattc gtgtataggg tgaccataac    12480
aaagtaccac agactgtgtg gtttaaacag caggaattta tcgtcacagt cctggagctg    12540
gaagtctcag atgaacgtgt ggggaggatt ggtttcttct gaggcctccc ttttggctt     12600 gtaggtggcc atcttgtccc tgtgccttca tatggtcttt cttctgtgca tgtctgtgtc    12660
ccaatttctt cttatgaaga cactagtcat gttggatttg gtttcacccg tatgacctca    12720
ttttccttaa tcacctctaa aggccctgtc ttccaataca gtcagagttg aggtattggg    12780
gctaggactt caacatatga attttgggg aacacaattc agcttgtaaa agtcacttat     12840
gagaagagtt taatgttagc ctctgagtga gtcagaattt aatgttaatt atgagtctaa    12900
atttaatgta aattctgagt gagtcagaat tagtgggtaa aaatttgaga cctcactttt    12960
taatgggcac acaaggaaga tggtgcatta gtaggtatct cctcaggtca ggctggatgt    13020
cattttaact cctaacaatt tatagcagca gccaggcaag caaaagtcaa tctggaaata    13080
cactgcctgc ctaaacagaa acacttaggt caatactata gctttcaaaa gggaaggtaa    13140
caccgtgtgc cctgggtgtg gttaatctgt aagaattttt aaaaccacaa gcttttcct    13200 ctacagtata ccccttctacc aacataattt gatgtatact tggggatgcc aattttttct    13260
taaaacatta actaaagaa agcctaagta aggaaacaac tttgttggct tttgtgccct     13320
ccaaacctga atgtattgct tctgaactgc tcagaatgtg gtttctgttg taatgaaggg    13380
gtactggctt acacattcac tgcacacatt aagcactggg aaggaaacag taggcaaaga    13440
ggtgggtttt tcctccttgt cttgtaggca tgtcggggaa accagcacga tgtgccagtc    13500
attcctttgg atgtagtaga taatcagaca gagaagttgg acaccaacat aactgaggtg    13560
gatgcagcct ccgtttacac gctgcctgct ggagctgact tcctcatgtg ttactctgtt    13620
gcagaaggtg tgtggtgttt aaaacaaaca tataattgcc tctcttggct aaggtcctgt    13680
aagtttcacc tttgattggt ttgggtcaga tctttcggtt gggacatggt gattccatcc    13740
tgaagctcac agacttagaa tttctttgac cacatggcac agagtgataa atgaaagtgt    13800
aaagtacctt acagaaaaat aattcctgag agttatgttg agtaaagcaa cagtctaatt    13860
aattatatta gtattagcag cctaccatca gttactgagg gtggtagtgc cattgtggta    13920
attgtcatgg aaagctttaa ttttttttttt ttttgagaca aggtctcaac tctgtcactg    13980
aggctgaagt gcaatggcat gatcatggct cactgcagcc tcaatttctc aggctcaagc    14040
aatcctccca cctcagcccc cctgtagctg ggactatagg catgcaccac catgcttggc    14100
```

```
taacttttta attttcggt agagattggg tcttgctatg ttgcccaggc tggtctcaaa    14160
caatcctcca gccttggcct cccaaagtgc tgggagtaca ggtatgagcc attgcgtgcg    14220
tgcgtgcgtt ttttttttt atagtctcac tctgttgccc agacgtgtgt gtgtgtgtgt    14280
attttttttt ttttaata gtctcactct gttgcccagg cgggagtgca gtggtccaat    14340
gtcagctcac tgcaacctct gcctcctggg ttcaagtgat tctcctacct cagcctcccg    14400
agtagctggg aatacaggtg cctgccacca cgccaagcta attttgtag ttttagtaga    14460 gatggggttt caccatgttg gccaggctgg tctcgaactc ctgacctcaa gtgatctgcc    14520
tgcctcagcc tcccaaagtg ctgggattat aggcatgagc caccatgccc aactgaaaaa    14580
tattttgata atggttcttt gcttttgtag taaataattt tgacttcttt ttagtaatct    14640
catgtctcaa tcattgtcta tcttgggaat ttttaggaa atggaagaaa ttatacagaa    14700
ttaaccccgt gtatataaaa ctatatagaa ttaatctctt ttcccatttg aaagagtca    14760 aaaaattta aagccattt atatcatgga cacatcttaa gactcttcta aggatttta    14820 agaacttata cttctgtaac taaaagaat acacacagta attgaaagcc agaaactgc    14880 agcaacattt tccttctcac tttttagga tattattctc accgggaaac tgtgaacggc    14940
tcatggtaca ttcaagattt gtgtgagatg ttgggaaaat atggctcctc cttagagttc    15000
acagaactcc tcacactggt gaacaggaaa gtttctcagc gccgagtgga cttttgcaaa    15060
gacccaagtg caattggaaa gaagcaggtt ccctgttttg cctcaatgct aactaaaaag    15120
ctgcatttct ttccaaaatc taattaatta atagaggcta tctaatttta cactctgtat    15180
tgaaaatggc tttctcagcc aggcgtggtt actcacacct gtaatcccag cactttggga    15240
gtccaaggtg ggcggatcac ctgaggtcgg gagttcgaga ccagcctgac caacatggag    15300 aagcccgtc tctactaaaa atgcaaaaaa aatttagct aggcatggcg gcgcatgcct    15360
gcaatcccag ctacttggaa ggctgaggca ggagaatcac ttgaacccag gaggtggagg    15420
ctgcggtgag ccgagattgc gccattgcac tccagcctgg gcaacgagtg aaactccgtc    15480
tcaaaaaaaa gaaaatgtct ttctcttcct tttatataaa tatcgttagg gtgaagcatt    15540
atggtctaat gattcaaatg ttttaaagtt taatgcctag cagagaactg ccttaaaaaa    15600 aaaaaaaaa agttcatgtt ggccatggtg aaagggttg tatggagaa acaaaatcct    15660 caggaaatta gataaataaa aatttataag catttgtatt attttttaat aaactgcagg    15720
gttacacaaa aatctagctg atttaacttg tattttgtca cttttttata aagtttatt    15780 gtttgatgtt ttaaaggtt tttgaaatcc aggaattaaa tcatccctta ataaatatt    15840 cgaaattcat atttattac atttttctaa ctcacattct tgttcatttg tgtaattgat    15900
agatgttttt tactcggtca tttaaatgtt taatatttca tctacatatg aattaccaca    15960
ttttgtgtat gactttaatt cctactttaa aaaaatcag cattccagaa ttgttgtatg    16020
gcattctgag gatgaaatag aaaacataat tcttagccac tataggttga acacctgcaa    16080
aatctgattc tgtcagcatc ttccatgtta agttcctaca aacagtccaa cagtcatcag    16140
acccattcac acacaatcac attaatagaa taacagatgt tactttcaag gttcaattct    16200
tattaatatg atatagaatc tgaataatac tgttttgtta ataatctgcc agaggctgaa    16260
gaaagttaac tgttttggct tcgatacctg aaacttgtga tttgcaggtt caaaagcaat    16320
cgtttatata cactgtttca gttgaagttc aaaaagtacc aactatactt tatggttggt    16380
ggaacattta tgcctttttg ataaatgata aaaagatctt actcccaact actgcatatt    16440
```

-continued

```
aaaaaaagaa gttaatgaca agacgattcc gtgggaggtt gaggcaggag ggttgcttga    16500
gcccaggagt ttgatttggc aagacctggt ctctgatttt tttaaaagga tgattccaaa    16560
ttaagtctaa gaatggaagt gaatgccaag cacagaccct ttcacctcca catagagaat    16620
aaacgtggga caagctgaca aggatttta gctaacagca gccaccgttg ctttgataga    16680
cgcatacaag ccctttctaa cattagcaag tcataaaaat ccaaaaagta aaatctcag    16740 ttgagaactt caaacaatac ttctgttta caagaattta ataacaaaga ttaaacaatc    16800
aaaatgaacc atgggactca aaaacatcct aagttgcaaa atcaatacat aatgaaaat    16860 ctgacgacat ttaaaactgt aagattaatt cttttcattg agttcttcta cttgcatttg    16920
caaacagaga gaatgacgcg cctgtttcag ggattcttta gcctgtcatg ggaaaagaa    16980 aaagcatgtg atcagaaaga                                                17000
```

```
<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
cagttgacac tgccgggtgc                                                   20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
cttgccctcc tcttcctgaa                                                   20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
cgcgcagcca gacaccttgc                                                   20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
gccgagctca ttgcagccaa                                                   20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
tcttccccac ctgccgggtg                                                   20
```

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
tctcttttat agaaggcatc                                               20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
aaacatttct cttttataga                                               20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
tttctgccgg atcaaacatt                                               20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
aaacctgcgg gtaagattgt                                               20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
atctgaaaac ctgcgggtaa                                               20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
cctagatctg aaaacctgcg                                               20

<210> SEQ ID NO 30
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 30
caaatcctag atctgaaaac                                              20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
cacttcaaat cctagatctg                                              20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
catttcactt caaatcctag                                              20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
taaagcattt cacttcaaat                                              20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
cagtagttct tctgctttaa                                              20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
ttgagcagta gttcttctgc                                              20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
tgacacctca tgaattttga                                              20
```

```
<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
acagttgaca cctcatgaat                                               20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
aacagttgac acctcatgaa                                               20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
acacaaagca atcggcatct                                               20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
ccatggctca ggaagacaca                                               20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
ttagcatcat atgcataaat                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
aagccagtta atgtctgaat                                               20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 43
gtctcctttg aacaagccag                                               20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
acacttgtct cctttgaaca                                               20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
ttgggttttc caaccaggct                                               20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
atatcttggg ttttccaacc                                               20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
atgataaata tcttgggttt                                               20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
cctggatgat aaatatcttg                                               20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
cccgacatgc ctggatgata                                               20

<210> SEQ ID NO 50
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 50
tccaacttct ctgtctgatt                                              20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
gttggtgtcc aacttctctg                                              20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
ctcagttatg ttggtgtcca                                              20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
agtcagctcc agcaggcagc                                              20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
gagtaacaca tgaggaagtc                                              20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
tgcaacagag taacacatga                                              20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
```

```
ccttctgcaa cagagtaaca                                                    20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
gaataatatc cttctgcaac                                                    20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
cacacaaatc ttgaatgtac                                                    20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
ttctgtgaac tctaaggagg                                                    20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
ctgagaaact ttcctgttca                                                    20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
aacagggaac ctgcttcttt                                                    20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
attgaggcaa aacagggaac                                                    20

<210> SEQ ID NO 63
<211> LENGTH: 20
<212> TYPE: DNA
<213> ORGANISM: Artificial Sequence
```

<220> FEATURE:
<223> OTHER INFORMATION: Antisense Oligonucleotide

<400> SEQUENCE: 63
ttagcattga ggcaaaacag                                              20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
ttttagttag cattgaggca                                              20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
tgcagctttt tagttagcat                                              20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
cctctattaa ttaattagat                                              20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
gagtgtgaaa ttagatagcc                                              20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
cacgcctggc tgagaaagcc                                              20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
ctgggattac aggtgtgagt                                              20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
ccaaagtgct gggattacag                                                    20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
gcccaccttg gactcccaaa                                                    20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
tcaggtgatc cgcccacctt                                                    20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
ctggtctcga actcccgacc                                                    20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
ttggtcaggc tggtctcgaa                                                    20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
gcatttttag tagaggcggg                                                    20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 76
agccttccaa gtagctggga                                               20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
ccataatgct tcaccctaac                                               20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
gttctctgct aggcattaaa                                               20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
taaggcagtt ctctgctagg                                               20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
accatggcca acatgaactt                                               20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
caaatgctta taaattttta                                               20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82 agattttttgt gtaaccctgc                                              20

<210> SEQ ID NO 83
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
aggaggtgac agctgcattt                                              20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
gttttcttcc ccacctatta                                              20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
cagctttacc ttttatagaa                                              20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
aaacatttct ctgttaatga                                              20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
aactactacc tgcgggtaag                                              20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
tcttaaggga ggctgcatca                                              20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
```

```
atctgaaaac ctagtggtat                                              20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
actacctacc ctcatgaatt                                              20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
acagttgaca ctataaagga                                              20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
acaagtcata tgctggctct                                              20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
aggcaggcag tgtatttcca                                              20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
cctctttgcc tactgtttcc                                              20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
catatgtaga tgaaatatta                                              20

<210> SEQ ID NO 96
<211> LENGTH: 20
<212> TYPE: DNA
```

<210> SEQ ID NO 97
<211> LENGTH: 493
<212> TYPE: DNA
<213> ORGANISM: Artificial Sequence
<220> FEATURE:
<223> OTHER INFORMATION: Antisense Oligonucleotide

<400> SEQUENCE: 96
ttgtcagctt gtcccacgtt                                                    20

<210> SEQ ID NO 97
<211> LENGTH: 493
<212> TYPE: DNA
<213> ORGANISM: Mus musculus

<400> SEQUENCE: 97
gcaggaaacg ggtggacgag cggaggcctc agggctagga caccggtggg agctcgcggg        60
caggtgaaag taaaacatga cagaaaccga tggcttctac aaaagtaggg aagtgttcga      120
tccagccgag cagtacaaga tggaccacaa gaggagagga gttgccctca tcttcaatca      180
cgagaggttc ttttggcacc tgaccctccc agagaggcgg ggcaccaacg cagacagaga      240
caacctgact cgcaggtttt cagatctagg atttgaagtg aaatgcttta acgacctcag      300
agcagaagaa ctcctgctca aaattcacga ggtgtcgact tcaagccaca tagatgccga      360
ttgcttcatc tgtgtcttcc tgagccatgg ggaaggcaac cacgtttacg catacgacgc      420
caaaattgaa attcagacgt tgactggctt gttcaaagga gacaagtgtc agagcctggt      480
tggaaaccca aga                                                         493

<210> SEQ ID NO 98
<211> LENGTH: 472
<212> TYPE: DNA
<213> ORGANISM: Mus musculus

<400> SEQUENCE: 98
accccatcaa tgtaaactgc tcaattttgt agatgccata gaaaagtaat gttttatatt       60
tgttactttt caatcatgtt ggacgtggtg gaagggctaa aataatcct caggaaatta      120 ctatgcatca atgtctacta catttattac attttttagta aactgtaaga ttactctaaa    180
taccaactac tttgcctccc cttttgtgac actgtttata tgagtttact gtataatgtt     240
tgtaaagact tttgaaactc tagactgaga ttgttttcgc gtaataaaat gtctaagaac     300
tcattgacac tttctaattc ctatgtttat gtgatttata gtgggcctat ttgacttggt     360
catgtattca tttactatct tgtttacctc taatcaaggt aaactttata tgtggcttta     420
attcccattt tggaaacaat aaactttcca gaattaaaaa aaaaaaaaa aa              472

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
ttactttcac ctgcccgcga                                                   20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
ccctactttt gtagaagcca                                              20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
cttgtactgc tcggctggat                                              20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
tccatcttgt actgctcggc                                              20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
ttgtggtcca tcttgtactg                                              20

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104
tctcctcttg tggtccatct                                              20

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105
gattgaagat gagggcaact                                              20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
aacctctcgt gattgaagat                                              20

<210> SEQ ID NO 107
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 107
gtgccccgcc tctctgggag                                               20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
ggtcgttaaa gcatttcact                                               20

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109
ttgagcagga gttcttctgc                                               20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110
gaagtcgaca cctcgtgaat                                               20

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
atcggcatct atgtggcttg                                               20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
ctcaggaaga cacagatgaa                                               20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
gtatgcgtaa acgtggttgc                                               20
```

```
<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
gtctgaattt caattttggc                                              20

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
tcctttgaac aagccagtca                                              20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116
ggctctgaca cttgtctcct                                              20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
caaccaggct ctgacacttg                                              20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
ttttccaacc aggctctgac                                              20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
ccccgacagg cctggatgat                                              20

<210> SEQ ID NO 120
<211> LENGTH: 20
<212> TYPE: DNA
<213> ORGANISM: Artificial Sequence
<220> FEATURE:
```

<223> OTHER INFORMATION: Antisense Oligonucleotide

<400> SEQUENCE: 120
cgggtacgtc atgctggcta                    20

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121
ccagcttgtc tgtctggtga                    20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
tccacctggg tcacgttgtc                    20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
gcagcatcca cctgggtcac                    20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124
gtgtacacgg acgcagcatc                    20

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
ggaagtctgc ccctgccggc                    20

<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126
cttctgcgac agagtagcac                    20

```
<210> SEQ ID NO 127
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 127
gtgagagtaa tacccttctg                                              20

<210> SEQ ID NO 128
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 128
attcacagtt tctcggtgag                                              20

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
aatgtaccag gagccattca                                              20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130
aatcctgaat gtaccaggag                                              20

<210> SEQ ID NO 131
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 131
tgaactccag ggaactgccg                                              20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
gcgtgagcag ctccgtgaac                                              20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 133
gttcaccagc gtgagcagct                                          20

<210> SEQ ID NO 134
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 134
tgcatccggg tctttgcaga                                          20

<210> SEQ ID NO 135
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135 cttttggtc agcattgagg                                           20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
atgcagcttt ttggtcagca                                          20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
gggacagaaa tgcagctttt                                          20

<210> SEQ ID NO 138
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138
ctaggtttgg gacagaaatg                                          20

<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139
accagctggc ctttgtataa                                          20

<210> SEQ ID NO 140
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 140
tgggtgaaag tcttccacca                                              20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
tgaagcagtt tacattgatg                                              20

<210> SEQ ID NO 142
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142
ggcatctaca aaattgaagc                                              20

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
ttctatggca tctacaaaat                                              20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 144
aacattactt ttctatggca                                              20

<210> SEQ ID NO 145
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 145
cacgtccaac atgattgaaa                                              20

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146
```

```
cttccaccac gtccaacatg                                              20

<210> SEQ ID NO 147
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 147
ttatttttag cccttccacc                                              20

<210> SEQ ID NO 148
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 148
tagtagacat tgatgcatag                                              20

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
taataaatgt agtagacatt                                              20

<210> SEQ ID NO 150
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 150
tacagtttac taaaaatgta                                              20

<210> SEQ ID NO 151
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 151
gtaatcttac agtttactaa                                              20

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
agttggtatt tagagtaatc                                              20

<210> SEQ ID NO 153
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 153
ggcaaagtag ttggtattta                                          20

<210> SEQ ID NO 154
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 154
ctttacaaac attatacagt                                          20

<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 155
aaaacaatct cagtctagag                                          20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156
cgcgaaaaca atctcagtct                                          20

<210> SEQ ID NO 157
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 157
ttattacgcg aaaacaatct                                          20

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
tgaggcctcc gctcgtccac                                          20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
ccggtgtcct agccctgagg                                          20
```

```
<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160
aggcccacta taaatcacat                                                      20

<210> SEQ ID NO 161
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 161
ccttgattag aggtaaacaa                                                      20

<210> SEQ ID NO 162
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 162
ccaaaatggg aattaaagcc                                                      20

<210> SEQ ID NO 163
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 163
ttgtttccaa aatgggaatt                                                      20

<210> SEQ ID NO 164
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 164
aaaagtttat tgtttccaaa                                                      20
```

ANTISENSE MODULATION OF CASPASE 6 EXPRESSION

FIELD OF THE INVENTION

The present invention provides compositions and methods for modulating the expression of caspase 6. In particular, this invention relates to compounds, particularly oligonucleotides, specifically hybridizable with nucleic acids encoding caspase 6. Such compounds have been shown to modulate the expression of caspase 6.

BACKGROUND OF THE INVENTION

Apoptosis, or programmed cell death, is a naturally occurring process that has been strongly conserved during evolution to prevent uncontrolled cell proliferation. This form of cell suicide plays a crucial role in ensuring the development and maintenance of multicellular organisms by eliminating superfluous or unwanted cells. However, if this process goes awry becoming overstimulated, cell loss and degenerative disorders including neurological disorders such as Alzheimers, Parkinsons, ALS, retinitis pigmentosa and blood cell disorders can result. Stimuli which can trigger apoptosis include growth factors such as tumor necrosis factor (TNF), Fas and transforming growth factor beta (TGFβ), neurotransmitters, growth factor withdrawal, loss of extracellular matrix attachment and extreme fluctuations in intracellular calcium levels (Afford and Randhawa, *Mol. Pathol.*, 2000, 53, 55–63).

Alternatively, insufficient apoptosis, triggered by growth factors, extracellular matrix changes, CD40 ligand, viral gene products neutral amino acids, zinc, estrogen and androgens, can contribute to the development of cancer, autoimmune disorders and viral infections (Afford and Randhawa, *Mol. Pathol.*, 2000, 53, 55–63). Consequently, apoptosis is regulated under normal circumstances by the interaction of gene products that either induce or inhibit cell death and several gene products which modulate the apoptotic process have now been identified.

The most well-characterized apoptotic signaling cascade to date is that orchestrated by a family of cysteine proteases known as caspases. These enzymes activate apoptosis through proteolytic events triggered by one of several described mechanisms; including ligand binding to the cell surface death receptors of either the TNF or NGF receptor families, changes in mitochondrial integrity or chemical induction (Thornberry, *Br. Med. Bull.*, 1997, 53, 478–490).

Caspases have been classified into two groups, initiator caspases and effector caspases, based upon their position in the apoptotic signaling pathway.

Initiator caspases include caspase 1, 2, 4, 5, 8, 9, 10 and 14 and these enzymes have the largest prodomains of all the caspase zymogens. These prodomains allow the initiator caspases to interact with other downstream substrates including other caspases. Initiator caspases are further divided into two groups based on their protein binding domains. Caspases 8 and 10 contain the DED (death effector domain) while caspases 1, 2, 4 and 9 contain the CARD (caspase recruitment domain) (Bratton et al., *Exp. Cell. Res.*, 2000, 256, 27–33; Garcia-Calvo et al., *Cell. Death Differ.*, 1999, 6, 362–369).

Effector caspases are activated by initiator caspases and include caspase 3, 6, 7, 11 and 13 and these contain a shorter prodomain. Once activated, effector caspases then cleave a number of structural and regulatory proteins within the cell (Bratton et al., *Exp. Cell. Res.*, 2000, 256, 27–33; Garcia-Calvo et al., *Cell. Death Differ.*, 1999, 6, 362–369).

Caspase 6 (also known as CASP6, ced-3 homology 2 and MCH2) is an effector caspase first identified in Jurkat T lymphocytes. Characterization of the gene revealed that caspase 6 exists as two different isoforms, the longer of which induced apoptosis in Sf9 insect cells (Fernandes-Alnemri et al., *Cancer Res.*, 1995, 55, 2737–2742). These isoforms have been shown to have differential expression patterns suggesting different or alternate roles in apoptosis (Faleiro et al., *Embo J.*, 1997, 16, 2271–2281). In fact, the longer form of caspase 6, MCH2α, preferentially cleaves lamin A, an event required for nuclear reorganization during apoptosis (Orth et al., *J. Biol. Chem.*, 1996, 271, 16443–16446; Takahashi et al., *Proc. Natl. Acad. Sci. U.S.A.*, 1996, 93, 8395–8400).

Disclosed in U.S. Pat. No. 5,985,640 are the nucleotide and polypeptide sequence of the caspase 6 gene as well as the sequence of the splice variants thereof. Also generally disclosed are antisense oligonucleotides, at least 10 nucleotides in length, which hybridize with the caspase 6 mRNA. The antisense oligonucleotides include a single-stranded DNA sequence and an antisense RNA oligonucleotide produced from an expression vector within the cell (Litwack et al., 1999).

Caspase 6 has been localized to human chromosome 4q25, a region frequently affected in disorders such as Reiger syndrome, a dominantly inherited disorder characterized by hypodontia and malformation of the eye (Tiso et al., *Biochem. Biophys. Res. Commun.*, 1996, 225, 983–989). It has also been proposed that the protein product of a gene at this locus interacts with the ataxia telangiectasia gene product accounting for the genetic instability seen in this disorder. Caspase 6 has also been implicated in the inhibition of replicative DNA synthesis after certain insults such as ionizing radiation (Nasir et al., *Mamm. Genome*, 1997, 8, 56–59).

Increased expression of caspase 6 has been noted in several neoplastic disorders including gallbladder carcinomas and dysplasias (Turunen et al., *Histol. Histopathol.*, 2000, 15, 53–60), malignant non-Hodgkin's lymphoma (Soini and Paakko, *Apmis*, 1999, 107, 1043–1050), breast cancer (Vakkala et al., *Br. J. Cancer*, 1999, 81, 592–599) and osteosarcomas (Seki et al., *Cancer Chemother. Pharmacol.*, 2000, 45, 199–206).

In addition, caspase 6 has been shown to play a role in the processing of the amyloid precursor protein in Alzheimer's disease (LeBlanc et al., *J. Biol. Chem.*, 1999, 274, 23426–23436; Pellegrini et al., *J. Biol. Chem.*, 1999, 274, 21011–21016).

Collectively, these data suggest that modulation of caspase 6 would render opportunity to treat patients with various types of cancers or neurological conditions such as Alzheimer's disease as well as a variety of deregulated apoptotic pathologic conditions.

Several types of broad-spectrum caspase inhbitors have been identified for the treatment of deregulated bone metabolism (Harada et al., 2000; Reszka, 1999), as immunomodulatory agents (Gunasekera et al., 2000) and as combination therapies for the regulation of blood cholesterol (Reszka, 1999). These non-specific caspase inhibitors fall into three main classes; peptide-based molecules that mimic caspase substrates, small molecules and naturally-occurring caspase inhibitors or decoys (Deveraux et al., *Embo J.*, 1998, 17, 2215–2223; Dong et al., *Biochem. J.*, 2000, 347 Pt 3, 669–677; Gunasekera et al., 2000; Harada et al., 2000; Reszka, 1999; Reszka, 1999; Robidoux et al., 2000; Spruce et al., 1999).

Strategies aimed at modulating caspase 6 function have involved the use of antibodies and molecules that block upstream entities such as the death receptors and broad-spectrum caspase inhibitors.

Currently there exists a need to identify methods of modulating apoptosis for the therapeutic treatment of human diseases and it is believed that caspases modulators will be integral to these methods.

Antisense technology is emerging as an effective means for reducing the expression of specific gene products and may therefore prove to be uniquely useful in a number of therapeutic, diagnostic, and research applications for the modulation of gene expression and cellular processes.

There are no known therapeutic agents which effectively inhibit the synthesis of caspase 6 and the present invention provides compositions and methods for modulating caspase 6 expression, including modulation of aberrant forms of caspase 6, including alternatively spliced forms.

SUMMARY OF THE INVENTION

The present invention is directed to compounds, particularly antisense oligonucleotides, which are targeted to a nucleic acid encoding caspase 6, and which modulate the expression of caspase 6. Pharmaceutical and other compositions comprising the compounds of the invention are also provided. Further provided are methods of modulating the expression of caspase 6 in cells or tissues comprising contacting said cells or tissues with one or more of the antisense compounds or compositions of the invention. Further provided are methods of treating an animal, particularly a human, suspected of having or being prone to a disease or condition associated with expression of caspase 6 by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding caspase 6, ultimately modulating the amount of caspase 6 produced. This is accomplished by providing antisense compounds which specifically hybridize with one or more nucleic acids encoding caspase 6. As used herein, the terms "target nucleic acid" and "nucleic acid encoding caspase 6" encompass DNA encoding caspase 6, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of caspase 6. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding caspase 6. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding caspase 6, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'—5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular $—CH_2—NH—O—CH_2—$, $—CH_2—N(CH_3)—O—CH_2—$ [known as a methylene (methylimino) or MMI backbone], $—CH_2—O—N(CH_3)—CH_2—$, $—CH_2—N(CH_3)—N(CH_3)—CH_2—$ and $—O—N(CH_3)—CH_2—CH_2—$ [wherein the native phosphodiester backbone is represented as $—O—P—O—CH_2—$] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$, also described in examples hereinbelow.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methylene ($—CH_2—$)$_n$ group bridging the 2' oxygen atom and the 3' or 4' carbon atom wherein n is 1 or 2. LNAs and preparation thereof are described in WO 98/39352 and WO 99/14226.

Other preferred modifications include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal ucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluores-ceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al., *Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyloxycholesterol moiety (Crooke et al., *J. Pharmacol. Exp. Ther.*, 1996, 277, .923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos.: 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos.: 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of caspase 6 is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding caspase 6, enabling sandwich and other assays to easily be constructed to exploit this fact. Hybridization of the antisense oligonucleotides of the invention with a nucleic acid encoding caspase 6 can be detected by means known in the art. Such means may include conjugation of an enzyme to the oligonucleotide, radiolabelling of the oligonucleotide or any other suitable detection means. Kits using such detection means for detecting the level of caspase 6 in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g. p-amino), poly (methylcyanoacrylate), poly(ethylcyanoacrylate), poly (butylcyanoacrylate), poly(isobutylcyanoacrylate), poly (isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser No. 08/886,829 (filed Jul. 1, 1997), Ser No. 09/108,673 (filed Jul. 1, 1998), Ser No. 09/256,515 (filed Feb. 23, 1999), Ser No. 09/082,624 (filed May 21, 1998) and Ser No. 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to.those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 µm in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and triglycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P. Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or ore hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Ilium et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., J. Pharm. Pharmacol., 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther.*, 1992, 263, 25; Yamashita et al., *J. Pharm. Sci.*, 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J. Control Rel.*, 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers. Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. optimum dosages may vary depending on the relative potency of individual oligonucleotides, and can generally be estimated based on $EC_{50}$S found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis

Deoxy and 2'-Alkoxy Amidites

2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research*, 1993, 21, 3197–3203] using commercially available phosphoramidites (Glen Research, Sterling Va. or ChemGenes, Needham Mass.).

2'-Fluoro Amidites

2'-Fluorodeoxyadenosine Amidites

2'-fluoro oligonucleotides were synthesized as described previously [Kawasaki, et. al., *J. Med. Chem.*, 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabino-furanosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane (4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141

M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/hexane (1:1) containing 0.5% Et$_3$NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in CH$_2$Cl$_2$ (1 L) Tetrazole diisopropylamine (7.1 g) and 2-cyanoethoxy-tetra(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) Nucleoside Amidites and 2'-O-(Dimethylaminooxyethyl) Nucleoside Amidites 2'-(Dimethylaminooxyethoxy) nucleoside amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5-O-tert-Butyldiphenylsilyl-O$^2$-2-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160 ° C. was reached and then maintained for 16 h (pressure <100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over P$_2$O$_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-Butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.1 g, 4.5 mmol) was dissolved in dry CH$_2$Cl$_2$ (4.5 mL) and methylhydrazine (300 mL, 4.64 mmol) was added dropwise at −10° C. to 0° C. After 1 h the mixture was filtered, the filtrate was washed with ice cold CH₂Cl₂ and the combined organic phase was washed with water, brine and dried over anhydrous Na₂SO₄. The solution was concentrated to get 2'-O-(aminooxyethyl)thymidine, which was then dissolved in MeOH (67.5 mL). To this formaldehyde (20% aqueous solution, w/w, 1.1 eq.) was added and the resulting mixture was strirred for 1 h. Solvent was removed under vacuum; residue chromatographed to get 5'-O-tert-butyldiphenylsilyl-2'-O-[(2-formadoximinooxy)ethyl]-5-methyluridine as white foam (1.95 g, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy)ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in CH₂Cl₂). Aqueous NaHCO₃ solution (5%, 10 mL) was added and extracted with ethyl acetate (2×20 mL). Ethyl acetate phase was dried over anhydrous Na₂SO₄, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% NaHCO₃ (25 mL) solution was added and extracted with ethyl acetate (2×25 mL). Ethyl acetate layer was dried over anhydrous Na₂SO₄ and evaporated to dryness . The residue obtained was purified by flash column chromatography and eluted with 5% MeOH in CH₂Cl₂ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in CH₂Cl₂). Solvent was removed under vacuum and the residue placed on a flash column and eluted with 10% MeOH in CH₂Cl₂ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over P₂O₅ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in CH₂Cl₂ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over P₂O₅ under high vacuum overnight at 40° C. Then the reaction mixture was dissolved in anhydrous acetonitrile (8.4 mL) and 2-cyanoethyl-N,N,N¹,N¹-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous NaHCO₃ (40 mL). Ethyl acetate layer was dried over anhydrous Na₂SO₄ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) Nucleoside Amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-Isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-ethylacetyl)-51-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite].

2'-Dimethylaminoethoxyethoxy (2'-DMAEOE) Nucleoside Amidites

2'-dimethylaminoethoxyethoxy nucleoside amidites (also known in the art as 2'-O-dimethylaminoethoxyethyl, i.e., 2'-O—CH₂—O—CH₂—N(CH₂)₂, or 2'-DMAEOE nucleoside amidites) are prepared as follows. Other nucleoside amidites are prepared similarly.

2'-O-[2(2-N,N-Dimethylaminoethoxy)ethyl]-5-methyl Uridine

2[2-(Dimethylamino)ethoxy]ethanol (Aldrich, 6.66 g, 50 mmol) is slowly added to absolution of borane in tetrahydrofuran (1 M, 10 mL, 10 mmol) with stirring in a 100 mL bomb. Hydrogen gas evolves as the solid dissolves. $O^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-Dimethoxytrityl-2'-O-[2(2-N,N-dimethylaminoethoxy)ethyl)]-S-methyl Uridine

To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using MeOH:$CH_2Cl_2$:$Et_3$N (20:1, v/v, with 1% triethylamine) gives the title compound.
5'-O-Dimethoxytrityl-2'-O-[2(2-N,N-dimethylaminoethoxy)ethyl)]-5-methyl Uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAS) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]-[2'-deoxy]-[2'-O-(methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)phosphodiester]-[2'-deoxy Phosphorothioate]-[2'-O-(2-methoxyethyl)Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'—O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif. or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 5 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells:

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

b.END Cells:

The mouse brain endothelial cell line b.END was obtained from Dr. Werner Risau at the Max Plank Instititute (Bad Nauheim, Germany). b.END cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 3000 cells/well for use in RT-PCR analysis.

For Northern blotting or other analyses, cells may be seeded onto 100 mm or other standard tissue culture plates and treated similarly, using appropriate volumes of medium and oligonucleotide.

Treatment with Antisense Compounds:

When cells reached 80% confluency, they were treated with oligonucleotide. For cells grown in 96-well plates, wells were washed once with 200 μL OPTI-MEM™-1 reduced-serum medium (Gibco BRL) and then treated with 130 μL of OPTI-MEM™-1 containing 3.75 μg/mL LIPO-FECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Caspase 6 Expression

Antisense modulation of caspase 6 expression can be assayed in a variety of ways known in the art. For example, caspase 6 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of caspase 6 can be quantitated in a variety of ways well known in the art, such as immunoprecipitation, Western blot analysis (immunoblotting), ELISA or fluorescence-activated cell sorting (FACS). Antibodies directed to caspase 6 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Pro-* tocols in *Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1–11.2.22, John Wiley & Sons, Inc., 1991.

Example 11

Poly(A)+ mRNA Isolation

Poly(A)+ mRNA was isolated according to Miura et al., *Clin. Chem.*, 1996, 42, 1758–1764. Other methods for poly(A)+ mRNA isolation are taught in, for example, Ausubel, F. M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 µL cold PBS. 100 µL Buffer RLT was added to each well and the plate vigorously agitated for 20 seconds. 100 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 µL water into each well, incubating 1 minute, and then applying the vacuum for 30 seconds. The elution step was repeated with an additional 60 µL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of Caspase 6 mRNA Levels

Quantitation of caspase 6 mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 µL PCR cocktail (1×TAQMAN™ buffer A, 5.5 mM MgCl$_2$, 300 μM each of DATP, dCTP and dGTP, 600 μM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 μL total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen RNA quantification reagent from Molecular Probes. Methods of RNA quantification by RiboGreen™ are taught in Jones, L. J., et al, *Analytical Biochemistry*, 1998, 265, 368–374.

In this assay, 175 μL of RiboGreen™ working reagent (RiboGreen reagent diluted 1:2865 in 10 mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human caspase 6 were designed to hybridize to a human caspase 6 sequence, using published sequence information (GenBank accession number U20537, incorporated herein as SEQ ID NO:3). For human caspase 6 the PCR primers were: forward primer: AGGCTGAG-GCAGGAGAATCA (SEQ ID NO: 4) reverse primer: TGCAATGGCGCAATGCT (SEQ ID NO: 5) and the PCR probe was: FAM-TGAACCCAGGAGGTGGAGGCTGC-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were: forward primer: CAACGGATTTGGTCG-TATTGG (SEQ ID NO: 7) reverse primer: GGCAA-CAATATCCACTTTACCAGAGT (SEQ ID NO: 8) and the PCR probe was: 5' JOE-CGCCTGGTCACCAGGGCTGCT-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Probes and primers to mouse caspase 6 were designed to hybridize to a mouse caspase 6 sequence, using published sequence information (GenBank accession number Y13087, incorporated herein as SEQ ID NO:10). For mouse caspase 6 the PCR primers were: forward primer: AGCATGACG-TACCCGTGGTT (SEQ ID NO:11) reverse primer: GGT-CACGTTGTCCAGCTTGTC (SEQ ID NO: 12) and the PCR probe was: FAM-CCCTGGACATGGTGGATCACCAGAC-TAMRA (SEQ ID NO: 13) where FAM (PE-Applied Biosystems, Foster City, Calif.) is the fluorescent reporter dye) and TAMRA (PE-Applied Biosystems, Foster City, Calif.) is the quencher dye. For mouse GAPDH the PCR primers were: forward primer: GGCAAATTCAACGGCACAGT (SEQ ID NO: 14) reverse primer: GGGTCTCGCTCCTGGAAGCT (SEQ ID NO: 15) and the PCR probe was: 5' JOE-AAGGCCGAGAATGGGAAGCTTGTCATC-TAMRA 3' (SEQ ID NO: 16) where JOE (PE-Applied Biosystems, Foster City, Calif.) is the fluorescent reporter dye) and TAMRA (PE-Applied Biosystems, Foster City, Calif.) is the quencher dye.

Example 14

Northern Blot Analysis of Caspase 6 mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then robed using QUICKHYB™ hybridization solution (Stratagene, La Jolla, Calif.) using manufacturer's recommendations for stringent conditions.

To detect human caspase 6, a human caspase 6 specific probe was prepared by PCR using the forward primer AGGCTGAGGCAGGAGAATCA (SEQ ID NO: 4) and the reverse primer TGCAATGGCGCAATGCT (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

To detect mouse caspase 6, a mouse caspase 6 specific probe was prepared by PCR using the forward primer AGCATGACGTACCCGTGGTT (SEQ ID NO:11) and the reverse primer GGTCACGTTGTCCAGCTTGTC (SEQ ID NO: 12). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human Caspase 6 Expression by Chimeric Phosphorothioate Oligonucleotides having 2'-MOE Wings and a Deoxy Gap In accordance with the present invention, a series of oligonucleotides were designed to target different regions of the human caspase 6 RNA, using published sequences (GenBank accession-number U20537, incorporated herein as SEQ ID NO: 3, GenBank accession number U20536, incorporated herein as SEQ ID NO: 17, and the complement of residues 115001 to 132000 of GenBank accession number AC004067, incorporated herein as SEQ ID NO: 18). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynuceotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on human caspase 6 mRNA levels by quantitative real-time PCR as described in other examples herein. Data are averages from two experiments. If present, "N.D." indicates "no data".

TABLE 1

Inhibition of human caspase 6 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 134462 | Coding | 3 | 30 | cagttgacactgccgggtgc | 0 | 19 |
| 134463 | 5'UTR | 17 | 34 | cttgccctcctcttcctgaa | 0 | 20 |
| 134464 | 5'UTR | 17 | 49 | cgcgcagccagacaccttgc | 32 | 21 |
| 134465 | Start Codon | 17 | 70 | gccgagctcattgcagccaa | 0 | 22 |
| 134466 | Coding | 17 | 109 | tcttccccacctgccgggtg | 0 | 23 |
| 134467 | Coding | 17 | 145 | tctcttttatagaaggcatc | 0 | 24 |
| 134468 | Coding | 17 | 152 | aaacatttctcttttataga | 0 | 25 |
| 134469 | Coding | 17 | 165 | tttctgccggatcaaacatt | 55 | 26 |
| 134470 | Coding | 17 | 293 | aaacctgcgggtaagattgt | 49 | 27 |
| 134471 | Coding | 17 | 299 | atctgaaaacctgcgggtaa | 0 | 28 |
| 134472 | Coding | 17 | 304 | cctagatctgaaaacctgcg | 0 | 29 |
| 134473 | Coding | 17 | 309 | caaatcctagatctgaaaac | 0 | 30 |
| 134474 | Coding | 17 | 314 | cacttcaaatcctagatctg | 0 | 31 |
| 134475 | Coding | 17 | 319 | catttcacttcaaatcctag | 0 | 32 |
| 134476 | Coding | 17 | 324 | taaagcatttcacttcaaat | 0 | 33 |
| 134477 | Coding | 17 | 350 | cagtagttcttctgctttaa | 34 | 34 |
| 134478 | Coding | 17 | 355 | ttgagcagtagttcttctgc | 0 | 35 |
| 134479 | Coding | 17 | 371 | tgacacctcatgaattttga | 16 | 36 |
| 134480 | Coding | 17 | 376 | acagttgacacctcatgaat | 0 | 37 |
| 134481 | Coding | 17 | 377 | aacagttgacacctcatgaa | 0 | 38 |
| 134482 | Coding | 17 | 405 | acacaaagcaatcggcatct | 0 | 39 |
| 134483 | Coding | 17 | 424 | ccatggctcaggaagacaca | 0 | 40 |
| 134484 | Coding | 17 | 457 | ttagcatcatatgcataaat | 0 | 41 |
| 134485 | Coding | 17 | 484 | aagccagttaatgtctgaat | 26 | 42 |
| 134486 | Coding | 17 | 497 | gtctcctttgaacaagccag | a | 43 |
| 134487 | Coding | 17 | 503 | acacttgtctcctttgaaca | 0 | 44 |
| 134488 | Coding | 17 | 526 | ttgggttttccaaccaggct | 33 | 45 |
| 134489 | Coding | 17 | 531 | atatcttgggttttccaacc | 0 | 46 |
| 134490 | Coding | 17 | 538 | atgataaatatcttgggttt | 40 | 47 |
| 134491 | Coding | 17 | 543 | cctggatgataaatatcttg | 0 | 48 |
| 134492 | Coding | 17 | 552 | cccgacatgcctgatgata | 0 | 49 |
| 134493 | Coding | 17 | 616 | tccaacttctctgtctgatt | 43 | 50 |
| 134494 | Coding | 17 | 623 | gttggtgtccaacttctctg | 24 | 51 |
| 134495 | Coding | 17 | 632 | ctcagttatgttggtgtcca | 33 | 52 |
| 134496 | Coding | 17 | 675 | agtcagctccagcaggcagc | 1 | 53 |
| 134497 | Coding | 17 | 691 | gagtaacacatgaggaagtc | 0 | 54 |
| 134498 | Coding | 17 | 698 | tgcaacagagtaacacatga | 0 | 55 |
| 134499 | Coding | 17 | 703 | ccttctgcaacagagtaaca | 66 | 56 |
| 134500 | Coding | 17 | 712 | gaataatatccttctgcaac | 18 | 57 |
| 134501 | Coding | 17 | 759 | cacacaaatcttgaatgtac | 7 | 58 |
| 134502 | Coding | 17 | 800 | ttctgtgaactctaaggagg | 0 | 59 |
| 134503 | Coding | 17 | 833 | ctgagaaactttcctgttca | 7 | 60 |
| 134504 | Coding | 17 | 891 | aacagggaacctgcttcttt | 9 | 61 |
| 134505 | Coding | 17 | 901 | attgaggcaaaacagggaac | 0 | 62 |
| 134506 | Coding | 17 | 906 | ttagcattgaggcaaaacag | 5 | 63 |
| 134507 | Coding | 17 | 912 | ttttagttagcattgaggca | 0 | 64 |
| 134508 | Coding | 17 | 919 | tgcagcttttagttagcat | 0 | 65 |
| 134509 | Stop Codon | 17 | 951 | cctctattaattaattagat | 0 | 66 |
| 134510 | 3'UTR | 17 | 969 | gagtgtgaaattagatagcc | 0 | 67 |
| 134511 | 3'UTR | 17 | 1001 | cacgcctggctgagaaagcc | 0 | 68 |
| 134512 | 3'UTR | 17 | 1024 | ctgggattacaggtgtgagt | 45 | 69 |
| 134513 | 3'UTR | 17 | 1032 | ccaaagtgctgggattacag | 66 | 70 |
| 134514 | 3'UTR | 17 | 1047 | gcccaccttggactcccaaa | 19 | 71 |
| 134515 | 3'UTR | 17 | 1058 | tcaggtgatccgcccacctt | 66 | 72 |
| 134516 | 3'UTR | 17 | 1078 | ctggtctcgaactcccgacc | 49 | 73 |
| 134517 | 3'UTR | 17 | 1087 | ttggtcaggctggtctcgaa | 9 | 74 |
| 134518 | 3'UTR | 17 | 1119 | gcattttagtagaggcggg | 0 | 75 |
| 134519 | 3'UTR | 17 | 1179 | agccttccaagtagctggga | 33 | 76 |
| 134520 | 3'UTR | 17 | 1341 | ccataatgcttcaccctaac | 8 | 77 |
| 134521 | 3'UTR | 17 | 1385 | gttctctgctaggcattaaa | 4 | 78 |
| 134522 | 3'UTR | 17 | 1392 | taaggcagttctctgctagg | 0 | 79 |
| 134523 | 3'UTR | 17 | 1420 | accatggccaacatgaactt | 25 | 80 |
| 134524 | 3'UTR | 17 | 1487 | caaatgcttataaatttta | 63 | 81 |
| 134525 | 3'UTR | 17 | 1526 | agatttttgtgtaaccctgc | 4 | 82 |
| 134526 | Intron | 18 | 4828 | aggaggtgacagctgcattt | 29 | 83 |

TABLE 1-continued

Inhibition of human caspase 6 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 134527 | Intron | 18 | 6129 | gttttcttccccacctatta | 10 | 84 |
| 134528 | Exon | 18 | 6167 | cagcttaccttttatagaa | 61 | 85 |
| 134529 | Intron | 18 | 6699 | aaacatttctctgttaatga | 14 | 86 |
| 134530 | Exon | 18 | 6845 | aactactacctgcgggtaag | 28 | 87 |
| 134531 | Intron | 18 | 7359 | tcttaagggaggctgcatca | 0 | 88 |
| 134532 | Intron | 18 | 7981 | atctgaaaacctagtggtat | 66 | 89 |
| 134533 | Exon | 18 | 8057 | actacctaccctcatgaatt | 13 | 90 |
| 134534 | Intron | 18 | 9767 | acagttgacactataaagga | 0 | 91 |
| 134535 | Intron | 18 | 11327 | acaagtcatatgctggctct | 15 | 92 |
| 134536 | Intron | 18 | 13073 | aggcaggcagtgtatttcca | 15 | 93 |
| 134537 | Intron | 18 | 13423 | cctctttgcctactgtttcc | 0 | 94 |
| 134538 | Intron | 18 | 15931 | catatgtagatgaaatatta | 10 | 95 |
| 134539 | Intron | 18 | 16622 | ttgtcagcttgtcccacgtt | 0 | 96 |

As shown in Table 1, SEQ ID NOs 21, 26, 27, 34, 36, 42, 45, 47, 50, 51, 52, 56, 57, 69, 70, 71, 72, 73, 76, 80, 81, 83, 84, 85, 86, 87, 89, 90, 92, 93 and 95 demonstrated at least 10% inhibition of human caspase 6 expression in this assay and are therefore preferred. The target sites to which these preferred sequences are complementary are herein referred to as "active sites" and are therefore preferred sites for targeting by compounds of the present invention.

Example 16

Antisense Inhibition of Mouse Caspase 6 Expression by Chimeric Phosphorothioate Oligonucleotides Having 2'-MOE Wings and a Deoxy Gap In accordance with the present invention, a second series of oligonucleotides were designed to target different regions of the mouse caspase 6 RNA, using published sequences (GenBank accession number Y13087, incorporated herein as SEQ ID NO: 10, GenBank accession number W56965, incorporated herein as SEQ ID NO: 97, and GenBank accession number AW228920, the complement of which is incorporated herein as SEQ ID NO: 98). The oligonucleotides are shown in Table 2. "Target site" indicates the first (5'-most) nucleotide number on the particular target sequence to which the oligonucleotide binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on mouse caspase 6 mRNA levels by quantitative real-time PCR as described in other examples herein. Data are averages from two experiments. If present, "N.D." indicates "no data".

TABLE 2

Inhibition of mouse caspase 6 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 134472 | Coding | 10 | 199 | cctagatctgaaaacctgcg | 61 | 29 |
| 134473 | Coding | 10 | 204 | caaatcctagatctgaaaac | 55 | 30 |
| 134474 | Coding | 10 | 209 | cacttcaaatcctagatctg | 58 | 31 |
| 134475 | Coding | 10 | 214 | catttcacttcaaatcctag | 65 | 32 |
| 134476 | Coding | 10 | 219 | taaagcatttcacttcaaat | 67 | 33 |
| 134483 | Coding | 10 | 319 | ccatggctcaggaagacaca | 73 | 40 |
| 134486 | Coding | 10 | 392 | gtctcctttgaacaagccag | 82 | 43 |
| 134487 | Coding | 10 | 398 | acacttgtctcctttgaaca | 40 | 44 |
| 134488 | Coding | 10 | 421 | ttgggttttccaaccaggct | 73 | 45 |
| 134489 | Coding | 10 | 426 | atatcttgggttttccaacc | 64 | 46 |
| 134490 | Coding | 10 | 433 | atgataaatatcttgggttt | 30 | 47 |
| 134491 | Coding | 10 | 438 | cctggatgataaatatcttg | 45 | 48 |
| 134562 | 5'UTR | 10 | 2 | ttactttcacctgcccgcga | 39 | 99 |
| 134563 | Coding | 10 | 39 | ccctacttttgtagaagcca | 70 | 100 |
| 134564 | Coding | 10 | 68 | cttgtactgctcggctggat | 75 | 101 |
| 134565 | Coding | 10 | 73 | tccatcttgtactgctcggc | 86 | 102 |
| 134566 | Coding | 10 | 79 | ttgtggtccatcttgtactg | 64 | 103 |
| 134567 | Coding | 10 | 86 | tctcctcttgtggtccatct | 57 | 104 |
| 134568 | Coding | 10 | 108 | gattgaagatgagggcaact | 74 | 105 |
| 134569 | Coding | 10 | 118 | aacctctcgtgattgaagat | 74 | 106 |

TABLE 2-continued

Inhibition of mouse caspase 6 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 134570 | Coding | 10 | 154 | gtgccccgcctctctgggag | 59 | 107 |
| 134571 | Coding | 10 | 225 | ggtcgttaaagcatttcact | 78 | 108 |
| 134572 | Coding | 10 | 250 | ttgagcaggagttcttctgc | 56 | 109 |
| 134573 | Coding | 10 | 271 | gaagtcgacacctcgtgaat | 34 | 110 |
| 134574 | Coding | 10 | 290 | atcggcatctatgtggcttg | 72 | 111 |
| 134575 | Coding | 10 | 313 | ctcaggaagacacagatgaa | 58 | 112 |
| 134576 | Coding | 10 | 344 | gtatgcgtaaacgtggttgc | 59 | 113 |
| 134577 | Coding | 10 | 367 | gtctgaatttcaattttggc | 72 | 114 |
| 134578 | Coding | 10 | 389 | tcctttgaacaagccagtca | 9 | 115 |
| 134579 | Coding | 10 | 405 | ggctctgacacttgtctcct | 66 | 116 |
| 134580 | Coding | 10 | 411 | caaccaggctctgacacttg | 60 | 117 |
| 134581 | Coding | 10 | 416 | ttttcaaccaggctctgac | 68 | 118 |
| 134582 | Coding | 10 | 448 | ccccgacaggcctggatgat | 82 | 119 |
| 134583 | Coding | 10 | 468 | cgggtacgtcatgctggcta | 89 | 120 |
| 134584 | Coding | 10 | 510 | ccagcttgtctgtctggtga | 45 | 121 |
| 134585 | Coding | 10 | 529 | tccacctgggtcacgttgtc | 75 | 122 |
| 134586 | Coding | 10 | 535 | gcagcatccacctgggtcac | 77 | 123 |
| 134587 | Coding | 10 | 547 | gtgtacacggacgcagcatc | 61 | 124 |
| 134588 | Coding | 10 | 570 | ggaagtctgcccctgccggc | 75 | 125 |
| 134589 | Coding | 10 | 594 | cttctgcgacagagtagcac | 63 | 126 |
| 134590 | Coding | 10 | 608 | gtgagagtaataccttctg | 69 | 127 |
| 134591 | Coding | 10 | 623 | attcacagtttctcggtgag | 82 | 128 |
| 134592 | Coding | 10 | 638 | aatgtaccaggagccattca | 35 | 129 |
| 134593 | Coding | 10 | 645 | aatcctgaatgtaccaggag | 77 | 130 |
| 134594 | Coding | 10 | 687 | tgaactccagggaactgccg | 47 | 131 |
| 134595 | Coding | 10 | 702 | gcgtgagcagctccgtgaac | 21 | 132 |
| 134596 | Coding | 10 | 710 | gttcaccagcgtgagcagct | 55 | 133 |
| 134597 | Coding | 10 | 758 | tgcatccgggtctttgcaga | 68 | 134 |
| 134598 | Coding | 10 | 806 | cttttggtcagcattgagg | 68 | 135 |
| 134599 | Coding | 10 | 812 | atgcagcttttggtcagca | 89 | 136 |
| 134600 | Coding | 10 | 821 | gggacagaaatgcagctttt | 63 | 137 |
| 134601 | Coding | 10 | 829 | ctaggtttgggacagaaatg | 81 | 138 |
| 134602 | 3'UTR | 10 | 899 | accagctggcctttgtataa | 85 | 139 |
| 134603 | 3'UTR | 10 | 915 | tgggtgaaagtcttccacca | 83 | 140 |
| 134604 | 3'UTR | 10 | 933 | tgaagcagtttacattgatg | 83 | 141 |
| 134605 | 3'UTR | 10 | 947 | ggcatctacaaaattgaagc | 83 | 142 |
| 134606 | 3'UTR | 10 | 953 | ttctatggcatctacaaaat | 81 | 143 |
| 134607 | 3'UTR | 10 | 963 | aacattacttttctatggca | 77 | 144 |
| 134608 | 3'UTR | 10 | 997 | cacgtccaacatgattgaaa | 84 | 145 |
| 134609 | 3'UTR | 10 | 1004 | cttccaccacgtccaacatg | 75 | 146 |
| 134610 | 3'UTR | 10 | 1016 | ttattttagcccttccacc | 72 | 147 |
| 134611 | 3'UTR | 10 | 1050 | tagtagacattgatgcatag | 69 | 148 |
| 134612 | 3'UTR | 10 | 1059 | taataaatgtagtagacatt | 28 | 149 |
| 134613 | 3'UTR | 10 | 1077 | tacagtttactaaaaatgta | 29 | 150 |
| 134614 | 3'UTR | 10 | 1084 | gtaatcttacagtttactaa | 54 | 151 |
| 134615 | 3'UTR | 10 | 1098 | agttggtatttagagtaatc | 54 | 152 |
| 134616 | 3'UTR | 10 | 1106 | ggcaaagtagttggtattta | 80 | 153 |
| 134617 | 3'UTR | 10 | 1157 | ctttacaaacattatacagt | 62 | 154 |
| 134618 | 3'UTR | 10 | 1187 | aaaacaatctcagtctagag | 78 | 155 |
| 134619 | 3'UTR | 10 | 1191 | cgcgaaaacaatctcagtct | 81 | 156 |
| 134620 | 3'UTR | 10 | 1197 | ttattacgcgaaaacaatct | 68 | 157 |
| 134621 | 5'UTR | 97 | 12 | tgaggcctccgctcgtccac | 65 | 158 |
| 134622 | 5'UTR | 97 | 27 | ccggtgtcctagccctgagg | 73 | 159 |
| 134623 | 3'UTR | 98 | 329 | aggcccactataaatcacat | 76 | 160 |
| 134624 | 3'UTR | 98 | 380 | ccttgattagaggtaaacaa | 39 | 161 |
| 134625 | 3'UTR | 98 | 414 | ccaaaatgggaattaaagcc | 37 | 162 |
| 134626 | 3'UTR | 98 | 420 | ttgtttccaaaatgggaatt | 30 | 163 |
| 134627 | 3'UTR | 98 | 429 | aaaagtttattgtttccaaa | 36 | 164 |

As shown in Table 2, SEQ ID NOs 29, 30, 31, 32, 33, 40, 43, 44, 45, 46, 48, 99, 100, 101, 102, 103, 104, 105, 106, 107, 108, 109, 110, 111, 112, 113, 114, 116, 117, 118, 119, 120, 121, 122, 123, 124, 125, 126, 127, 128, 129, 130, 131, 133, 134, 135, 136, 137, 138, 139, 140, 141, 142, 143, 144, 145, 146, 147, 148, 151, 152, 153, 154, 155, 156, 157, 158, 159, 160, 161, 162, 163 and 164 demonstrated at least 30% inhibition of mouse caspase 6 expression in this experiment and are therefore preferred. The target sites to which these preferred sequences are complementary are herein referred to as "active sites" and are therefore preferred sites for targeting by compounds of the present invention.

Example 17

Western Blot Analysis of Caspase 6 Protein Levels

Western blot analysis (immunoblot analysis) is carried out using standard methods. Cells are harvested 16–20 h after oligonucleotide treatment, washed once with PBS, sus pended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to caspase 6 is used, with a radiolabelled or fluorescently labeled secondary antibody directed against the primary antibody species. Bands are visualized using a PHOSPHORIMAGER™ (Molecular Dynamics, Sunnyvale Calif.).

What is claimed is:

1. A compound 8 to 50 nucleobases in length targeted to a start codon region, a coding region, a stop codon region, or nucleobases 969 through 988, nucleobases 1001 through 1020, nucleobases 1024 through 1031, nucleobases 1058 through 1106, nucleobases 1119 through 1138, nucleobases 1179 through 1198, nucleobases 1341 throug 1360, nucleobases 1385 through 1411, nucleobases 1420 through 1439, nucleobases 1487 through 1506, or nucleobases 1526 through 1545 of a 3'-untranslated region of a nucleic acid molecule encoding human caspase 6 of SEQ ID NO: 17, nucleobases 4828 through 4847, nucleobases 6129 through 6148, nucleobases 6699 through 6718, nucleobases 7359 through 7378, nucleobases 7981 through 8000, nucleobases 9767 through 9786, nucleobases 11327 through 11346, nucleobases 13073 through 13092, nucleobases 13423 through 13442, nucleobases 15931 through 15950, or nucleobases 16622 through 16641 of an intron region or nucleobases 6167 through 6186, nucleobases 6845 through 6864, or nucleobases 8057 through 8076 of an exon region of a nucleic acid molecule encoding human caspase 6 of SEQ ID NO: 18, a coding region, a 5'-untranslated region, or a 3'-untranslated region of a nucleic acid molecule encoding mouse caspase 6 of SEQ ID NO: 10, a 5'-untranslated region of a nucleic acid molecule encoding mouse caspase 6 of SEQ ID NO: 97, or a 3'-untranslated region of a nucleic acid molecule encoding mouse caspase 6 of SEQ ID NO: 98, wherein said compound specifically hybridizes with one of said regions and inhibits the expression of caspase 6.

2. The compound of claim 1 which is an antisense oligonucleotide.

3. The compound of claim 2 wherein the antisense oligonucleotide comprises at least one modified internucleoside linkage.

4. The compound of claim 3 wherein the modified internucleoside linkage is a phosphorothioate linkage.

5. The compound of claim 2 wherein the antisense oligonucleotide comprises at least one modified sugar moiety.

6. The compound of claim 5 wherein the modified sugar moiety is a 2'-O-methoxyethyl sugar moiety.

7. The compound of claim 2 wherein the antisense oligonucleotide comprises at least one modified nucleobase.

8. The compound of claim 7 wherein the modified nucleobase is a 5-methylcytosine.

9. The compound of claim 2 wherein the antisense oligonucleotide is a chimeric oligonucleotide.

10. A composition comprising the compound of claim 1 and a pharmaceutically acceptable carrier or diluent.

11. The composition of claim 10 further comprising a colloidal dispersion system.

12. The composition of claim 10 wherein the compound is an antisense oligonucleotide.

13. A method of inhibiting the expression of caspase 6 in cells or tissues comprising contacting said cells or tissues in vitro with the compound of claim 1 so that expression of caspase 6 is inhibited.

* * * * *

UNITED STATES PATENT AND TRADEMARK OFFICE
CERTIFICATE OF CORRECTION

PATENT NO. : 6,566,135 B1
DATED : May 20, 2003
INVENTOR(S) : Andrew T. Watt

It is certified that error appears in the above-identified patent and that said Letters Patent is hereby corrected as shown below:

Title page,
Item [56], References Cited, OTHER PUBLICATIONS, please insert -- Afford et al., Apoptosis, Mol. Pathol., 2000, 53:55-63 --.

Signed and Sealed this

Fourth Day of May, 2004

JON W. DUDAS
*Acting Director of the United States Patent and Trademark Office*